United States Patent
Wang et al.

(10) Patent No.: US 9,333,218 B2
(45) Date of Patent: May 10, 2016

(54) MICRORNA COMPOSITIONS AND METHODS RELATED THERETO

(75) Inventors: Ya Wang, Decatur, GA (US); Baocheng Hu, Beijing (CN); Walter J. Curran, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/808,741

(22) PCT Filed: Jul. 14, 2011

(86) PCT No.: PCT/US2011/043960
§ 371 (c)(1),
(2), (4) Date: Jan. 7, 2013

(87) PCT Pub. No.: WO2012/009508
PCT Pub. Date: Jan. 19, 2012

(65) Prior Publication Data
US 2013/0109628 A1   May 2, 2013

Related U.S. Application Data

(60) Provisional application No. 61/364,666, filed on Jul. 15, 2010.

(51) Int. Cl.
| | |
|---|---|
| *C12N 15/11* | (2006.01) |
| *A61K 31/7105* | (2006.01) |
| *A61K 45/06* | (2006.01) |
| *C12N 15/113* | (2010.01) |
| *A61N 5/10* | (2006.01) |
| *C07H 21/02* | (2006.01) |

(52) U.S. Cl.
CPC .............. *A61K 31/7105* (2013.01); *A61K 45/06* (2013.01); *A61N 5/10* (2013.01); *C07H 21/02* (2013.01); *C12N 15/113* (2013.01); *C12N 2310/141* (2013.01); *C12N 2320/31* (2013.01)

(58) Field of Classification Search
CPC ........... C12N 15/113; C12N 2310/141; A61K 31/7105
See application file for complete search history.

(56) References Cited

U.S. PATENT DOCUMENTS

| | | | |
|---|---|---|---|
| 7,655,785 B1* | 2/2010 | Bentwich | 536/24.1 |
| 2009/0326051 A1* | 12/2009 | Corey et al. | 514/44 R |
| 2011/0144183 A1* | 6/2011 | Paquet et al. | 514/44 A |
| 2012/0302626 A1* | 11/2012 | Dave et al. | 514/44 A |

FOREIGN PATENT DOCUMENTS

| | | |
|---|---|---|
| EP | 2133431 | 12/2009 |
| WO | WO 2007/147409 A2 * | 12/2007 |
| WO | WO2008/061537 A2 * | 5/2008 |
| WO | 2009130479 | 10/2008 |
| WO | 2009143379 | 11/2009 |
| WO | WO2011/028550 A1 * | 3/2011 |

OTHER PUBLICATIONS

Inoue et al. PNAS 94,14584-14589,1997.*
Piriyapongsa et al. A Family of Human MicroRNA Genes from Miniature Inverted-Repeat Transposable Elements, 2007 PLoS ONE, Issue 2, e203.
Cummins et al. The colorectal microRNAome, 2006, Proc Natl Acad Sci U S A. 103:3687-3692.
Landfraf et al. A mammalian microRNA expression atlas based on small RNA library sequencing, 2007, Cell. Jun. 29, 2007; 129(7): 1401-1414.
Nishizaki et al. Synergistic Tumor Suppression by Coexpression of FHIT, 2004, Cancer Res 64:5745-5752.
Xu et al., Effect of fragile histidine triad gene transduction on proliferation and apoptosis of human hepatocellular carcinoma cells, World J Gastroenterol, 2008,14(23):3754-8.
Fortunato et al., Therapeutic Use of MicroRNAs in Lung Cancer 2014 Biomed Res Int. 2014:756975.
Hu et al., Identification of a tumor-suppressive human-specific microRNA within the FHIT tumor-suppressor gene, 2014 Cancer Res. 74(8):2283-94.

* cited by examiner

*Primary Examiner* — Brian Whiteman
(74) *Attorney, Agent, or Firm* — Emory Patent Group

(57) ABSTRACT

The disclosure relates to microRNAs (miRNAs) for the prophylaxis and/or treatment of neoplasia. The disclosure relates in particular to sequence corresponding to miR2 and the miR-548 family, including precursors, mature forms, fragments, and combinations thereof for the prophylaxis and/or treatment of neoplasias, particularly lung, stomach, and cervical cancer, alone or in combination with additional cancer treatments and therapeutics.

10 Claims, 9 Drawing Sheets

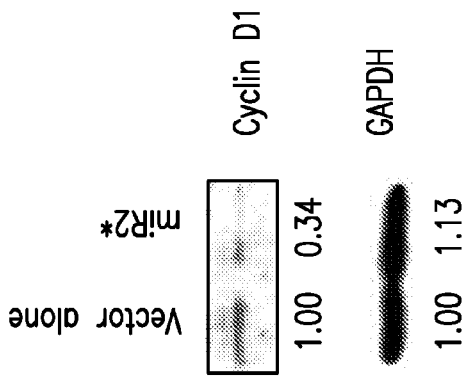
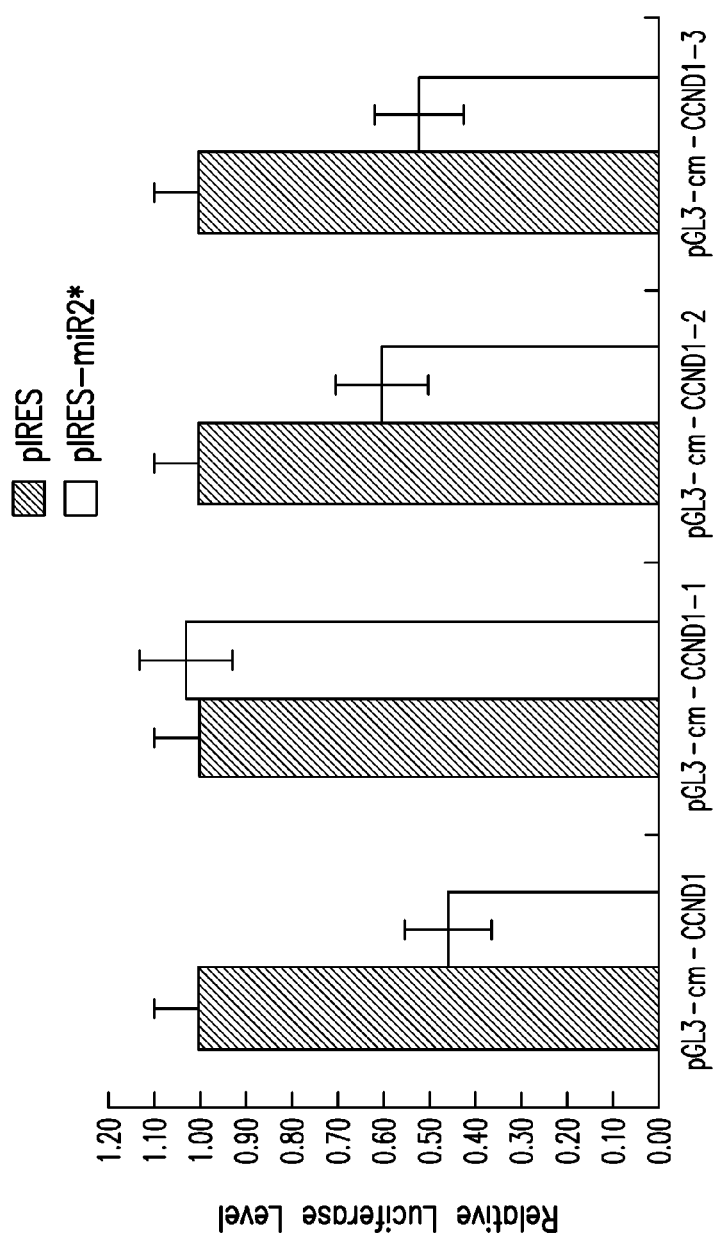
FIG. 14D
FIG. 14C

SEQUENCE LISTING

<160> NUMBER OF SEQ ID NOS: 76

<210> SEQ ID NO 1
<211> LENGTH: 65
<212> TYPE: DNA
<213> ORGANISM: Artificial Sequence
<220> FEATURE:
<223> OTHER INFORMATION: miR2 variant

<400> SEQUENCE: 1
ttagattggt gcaaagtaac tatggttttt gcccaaaaac catagttact tttgcaccaa    60
gctaa                                                                    65

<210> SEQ ID NO 2
<211> LENGTH: 21
<212> TYPE: DNA
<213> ORGANISM: Artificial Sequence
<220> FEATURE:
<223> OTHER INFORMATION: miR2 variant

<400> SEQUENCE: 2
aaaagtaact atggttttg c                                                   21

<210> SEQ ID NO 3
<211> LENGTH: 66
<212> TYPE: DNA
<213> ORGANISM: Artificial Sequence
<220> FEATURE:
<223> OTHER INFORMATION: miR2 variant

<400> SEQUENCE: 3
uuagauuggu gcaaaaguaa cuauggusuu ugcccaaaaa ccauaguuac uuuugcacca        60
agcuaa                                                                   66

<210> SEQ ID NO 4
<211> LENGTH: 21
<212> TYPE: DNA
<213> ORGANISM: Artificial Sequence
<220> FEATURE:
<223> OTHER INFORMATION: synthetic

<400> SEQUENCE: 4
aaaaguaacu augguuuuug c                                                  21

<210> SEQ ID NO 5
<211> LENGTH: 51
<212> TYPE: DNA
<213> ORGANISM: Artificial Sequence
<220> FEATURE:
<223> OTHER INFORMATION: synthetic

<400> SEQUENCE: 5
tgcgagcaca gaattaatac gactcactat aggtttttt ttttttttttt t                 51

<210> SEQ ID NO 6
<211> LENGTH: 3
<212> TYPE: DNA
<213> ORGANISM: Artificial Sequence
<220> FEATURE:
<223> OTHER INFORMATION: synthetic

<400> SEQUENCE: 6 aaa                                                                       3

<210> SEQ ID NO 7
<211> LENGTH: 4
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is a, c, g, t or u

<400> SEQUENCE: 7 aaan                                                                             4

<210> SEQ ID NO 8
<211> LENGTH: 3
<212> TYPE: DNA
<213> ORGANISM: Artificial Sequence
<220> FEATURE:
<223> OTHER INFORMATION: synthetic

<400> SEQUENCE: 8 uuu                                                                              3

<210> SEQ ID NO 9
<211> LENGTH: 4
<212> TYPE: DNA
<213> ORGANISM: Artificial Sequence
<220> FEATURE:
<223> OTHER INFORMATION: synthetic

<400> SEQUENCE: 9 uuug                                                                             4

<210> SEQ ID NO 10
<211> LENGTH: 6
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n is c or g

<400> SEQUENCE: 10 aaaanu                                                                           6

<210> SEQ ID NO 11
<211> LENGTH: 6
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n is c or u

<400> SEQUENCE: 11 uuuugn                                                                           6

<210> SEQ ID NO 12
<211> LENGTH: 5
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is a, c, g, t or u

<400> SEQUENCE: 12 aaanu                                                                            5

<210> SEQ ID NO 13
<211> LENGTH: 5
<212> TYPE: DNA
<213> ORGANISM: Artificial Sequence

```
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is a, c, g, t or u

<400> SEQUENCE: 13 aaant                                                                    5

<210> SEQ ID NO 14
<211> LENGTH: 5
<212> TYPE: DNA
<213> ORGANISM: Artificial Sequence
<220> FEATURE:
<223> OTHER INFORMATION: synthetic

<400> SEQUENCE: 14 uuugy                                                                    5

<210> SEQ ID NO 15
<211> LENGTH: 6
<212> TYPE: DNA
<213> ORGANISM: Artificial Sequence
<220> FEATURE:
<223> OTHER INFORMATION: miR2
<220> FEATURE:
<221> NAME/KEY: misc_feature
<222> LOCATION: (5)..(5)
<223> OTHER INFORMATION: n is a, c, g, t or u

<400> SEQUENCE: 15 aaaanu                                                                   6

<210> SEQ ID NO 16
<211> LENGTH: 6
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n is a, c, g, t or u

<400> SEQUENCE: 16 aaaant                                                                   6

<210> SEQ ID NO 17
<211> LENGTH: 6
<212> TYPE: DNA
<213> ORGANISM: Artificial Sequence
<220> FEATURE:
<223> OTHER INFORMATION: synthetic

<400> SEQUENCE: 17 uuuugy                                                                   6

<210> SEQ ID NO 18
<211> LENGTH: 22
<212> TYPE: DNA
<213> ORGANISM: Artificial Sequence
<220> FEATURE:
<223> OTHER INFORMATION: miR-548 variant

<400> SEQUENCE: 18
caaaacuggc aauuacuuuu gc                                                22
```

```
<210> SEQ ID NO 19
<211> LENGTH: 22
<212> TYPE: DNA
<213> ORGANISM: Artificial Sequence
<220> FEATURE:
<223> OTHER INFORMATION: miR-548 variant

<400> SEQUENCE: 19
aaaaguaauu gugguuuugg cc                                              22

<210> SEQ ID NO 20
<211> LENGTH: 22
<212> TYPE: DNA
<213> ORGANISM: Artificial Sequence
<220> FEATURE:
<223> OTHER INFORMATION: miR-548 variant

<400> SEQUENCE: 20
caaaacuggc aauuacuuuu gc                                              22

<210> SEQ ID NO 21
<211> LENGTH: 22
<212> TYPE: DNA
<213> ORGANISM: Artificial Sequence
<220> FEATURE:
<223> OTHER INFORMATION: miR-548 variant

<400> SEQUENCE: 21
aaaaguaauu gcgaguuuua cc                                              22

<210> SEQ ID NO 22
<211> LENGTH: 22
<212> TYPE: DNA
<213> ORGANISM: Artificial Sequence
<220> FEATURE:
<223> OTHER INFORMATION: miR-548 variant

<400> SEQUENCE: 22
aaaaguaauu gcgguuuuug cc                                              22

<210> SEQ ID NO 23
<211> LENGTH: 22
<212> TYPE: DNA
<213> ORGANISM: Artificial Sequence
<220> FEATURE:
<223> OTHER INFORMATION: miR-548 variant

<400> SEQUENCE: 23
aaaaguaauu gugguuuuug cc                                              22

<210> SEQ ID NO 24
<211> LENGTH: 22
<212> TYPE: DNA
<213> ORGANISM: Artificial Sequence
<220> FEATURE:
<223> OTHER INFORMATION: miR-548 variant

<400> SEQUENCE: 24
aaaaguaauu gugguuuuug cc                                              22

<210> SEQ ID NO 25
<211> LENGTH: 22
<212> TYPE: DNA
<213> ORGANISM: Artificial Sequence
<220> FEATURE:
<223> OTHER INFORMATION: miR-548 variant
```

```
<400> SEQUENCE: 25
aaaaacugag acuacuuuug ca                                              22

<210> SEQ ID NO 26
<211> LENGTH: 22
<212> TYPE: DNA
<213> ORGANISM: Artificial Sequence
<220> FEATURE:
<223> OTHER INFORMATION: miR-548 variant

<400> SEQUENCE: 26
aaaaguaauu gcggucuuug gu                                              22

<210> SEQ ID NO 27
<211> LENGTH: 22
<212> TYPE: DNA
<213> ORGANISM: Artificial Sequence
<220> FEATURE:
<223> OTHER INFORMATION: miR-548 variant

<400> SEQUENCE: 27
aaaaguacuu gcggauuuug cu                                              22

<210> SEQ ID NO 28
<211> LENGTH: 22
<212> TYPE: DNA
<213> ORGANISM: Artificial Sequence
<220> FEATURE:
<223> OTHER INFORMATION: miR-548 variant

<400> SEQUENCE: 28
aaaaguauuu gcggguuuug uc                                              22

<210> SEQ ID NO 29
<211> LENGTH: 19
<212> TYPE: DNA
<213> ORGANISM: Artificial Sequence
<220> FEATURE:
<223> OTHER INFORMATION: miR-548 variant

<400> SEQUENCE: 29
aaaaacugua auuacuuuu                                                  19

<210> SEQ ID NO 30
<211> LENGTH: 19
<212> TYPE: DNA
<213> ORGANISM: Artificial Sequence
<220> FEATURE:
<223> OTHER INFORMATION: miR-548 variant

<400> SEQUENCE: 30
aaaaacugua auuacuuuu                                                  19

<210> SEQ ID NO 31
<211> LENGTH: 19
<212> TYPE: DNA
<213> ORGANISM: Artificial Sequence
<220> FEATURE:
<223> OTHER INFORMATION: miR-548 variant

<400> SEQUENCE: 31
aaaaacugua auuacuuuu                                                  19

<210> SEQ ID NO 32
```

```
<211> LENGTH: 19
<212> TYPE: DNA
<213> ORGANISM: Artificial Sequence
<220> FEATURE:
<223> OTHER INFORMATION: miR-548 variant

<400> SEQUENCE: 32
aaaaacugua auuacuuuu                                              19

<210> SEQ ID NO 33
<211> LENGTH: 19
<212> TYPE: DNA
<213> ORGANISM: Artificial Sequence
<220> FEATURE:
<223> OTHER INFORMATION: miR-548 variant

<400> SEQUENCE: 33
aaaaacugua auuacuuuu                                              19

<210> SEQ ID NO 34
<211> LENGTH: 22
<212> TYPE: DNA
<213> ORGANISM: Artificial Sequence
<220> FEATURE:
<223> OTHER INFORMATION: miR-548 variant

<400> SEQUENCE: 34
aaaacuguaa uuacuuuugu ac                                          22

<210> SEQ ID NO 35
<211> LENGTH: 22
<212> TYPE: DNA
<213> ORGANISM: Artificial Sequence
<220> FEATURE:
<223> OTHER INFORMATION: miR-548 variant

<400> SEQUENCE: 35
caaaaguaau uuggauuuu gu                                           22

<210> SEQ ID NO 36
<211> LENGTH: 21
<212> TYPE: DNA
<213> ORGANISM: Artificial Sequence
<220> FEATURE:
<223> OTHER INFORMATION: miR-548 variant

<400> SEQUENCE: 36
caaagguauu ugugguuuuu g                                           21

<210> SEQ ID NO 37
<211> LENGTH: 22
<212> TYPE: DNA
<213> ORGANISM: Artificial Sequence
<220> FEATURE:
<223> OTHER INFORMATION: miR-548 variant

<400> SEQUENCE: 37
ccaaaacugc aguuacuuuu gc                                          22

<210> SEQ ID NO 38
<211> LENGTH: 22
<212> TYPE: DNA
<213> ORGANISM: Artificial Sequence
<220> FEATURE:
<223> OTHER INFORMATION: miR-548 variant

<400> SEQUENCE: 38
```

-continued aaaaguaauc gcgguuuuug uc                                                22

<210> SEQ ID NO 39
<211> LENGTH: 22
<212> TYPE: DNA
<213> ORGANISM: Artificial Sequence
<220> FEATURE:
<223> OTHER INFORMATION: miR-548 variant

<400> SEQUENCE: 39
aaaaguaauc gcgguuuuug uc                                                22

<210> SEQ ID NO 40
<211> LENGTH: 22
<212> TYPE: DNA
<213> ORGANISM: Artificial Sequence
<220> FEATURE:
<223> OTHER INFORMATION: miR-548 variant

<400> SEQUENCE: 40
aaaaguaauc gcgguuuuug uc                                                22

<210> SEQ ID NO 41
<211> LENGTH: 22
<212> TYPE: DNA
<213> ORGANISM: Artificial Sequence
<220> FEATURE:
<223> OTHER INFORMATION: miR-548 variant

<400> SEQUENCE: 41
aaaaguaauc gcgguuuuug uc                                                22

<210> SEQ ID NO 42
<211> LENGTH: 22
<212> TYPE: DNA
<213> ORGANISM: Artificial Sequence
<220> FEATURE:
<223> OTHER INFORMATION: miR-548 variant

<400> SEQUENCE: 42
uagcaaaaac ugcaguuacu uu                                                22

<210> SEQ ID NO 43
<211> LENGTH: 0
<212> TYPE: DNA
<213> ORGANISM: Artificial Sequence
<220> FEATURE:
<223> OTHER INFORMATION: miR-548 variant

<400> SEQUENCE: 43

000

<210> SEQ ID NO 44
<211> LENGTH: 22
<212> TYPE: DNA
<213> ORGANISM: Artificial Sequence
<220> FEATURE:
<223> OTHER INFORMATION: miR-548 variant

<400> SEQUENCE: 44
aaaaguaauu gcggauuuug cc                                                22

<210> SEQ ID NO 45
<211> LENGTH: 22
<212> TYPE: DNA

```
<213> ORGANISM: Artificial Sequence
<220> FEATURE:
<223> OTHER INFORMATION: miR-548 variant

<400> SEQUENCE: 45
aaaaguaauu gcggauuuug cc                                              22

<210> SEQ ID NO 46
<211> LENGTH: 22
<212> TYPE: DNA
<213> ORGANISM: Artificial Sequence
<220> FEATURE:
<223> OTHER INFORMATION: miR-548 variant

<400> SEQUENCE: 46
aaaaguaauu gcggauuuug cc                                              22

<210> SEQ ID NO 47
<211> LENGTH: 22
<212> TYPE: DNA
<213> ORGANISM: Artificial Sequence
<220> FEATURE:
<223> OTHER INFORMATION: miR-548 variant

<400> SEQUENCE: 47
aaaaguaauu gcggauuuug cc                                              22

<210> SEQ ID NO 48
<211> LENGTH: 22
<212> TYPE: DNA
<213> ORGANISM: Artificial Sequence
<220> FEATURE:
<223> OTHER INFORMATION: miR-548 variant

<400> SEQUENCE: 48
gcuggugcaa aaguaauggc gg                                              22

<210> SEQ ID NO 49
<211> LENGTH: 23
<212> TYPE: DNA
<213> ORGANISM: Artificial Sequence
<220> FEATURE:
<223> OTHER INFORMATION: miR-548 variant

<400> SEQUENCE: 49
auggccaaaa cugcaguuau uuu                                             23

<210> SEQ ID NO 50
<211> LENGTH: 21
<212> TYPE: DNA
<213> ORGANISM: Artificial Sequence
<220> FEATURE:
<223> OTHER INFORMATION: miR-548 variant

<400> SEQUENCE: 50
caaaagugau cgugguuuuu g                                               21

<210> SEQ ID NO 51
<211> LENGTH: 23
<212> TYPE: DNA
<213> ORGANISM: Artificial Sequence
<220> FEATURE:
<223> OTHER INFORMATION: miR-548 variant

<400> SEQUENCE: 51
caaagacugc aauuacuuuu gcg                                             23
```

```
<210> SEQ ID NO 52
<211> LENGTH: 22
<212> TYPE: DNA
<213> ORGANISM: Artificial Sequence
<220> FEATURE:
<223> OTHER INFORMATION: miR-548 variant

<400> SEQUENCE: 52
agcuacaguu acuuuugcac ca                                              22

<210> SEQ ID NO 53
<211> LENGTH: 23
<212> TYPE: DNA
<213> ORGANISM: Artificial Sequence
<220> FEATURE:
<223> OTHER INFORMATION: miR-548 variant

<400> SEQUENCE: 53
aaaaguaacu gcgguuuuug ccu                                             23

<210> SEQ ID NO 54
<211> LENGTH: 20
<212> TYPE: DNA
<213> ORGANISM: Artificial Sequence
<220> FEATURE:
<223> OTHER INFORMATION: miR-548 variant

<400> SEQUENCE: 54
uaaaaacugc aauuacuuuc                                                 20

<210> SEQ ID NO 55
<211> LENGTH: 22
<212> TYPE: DNA
<213> ORGANISM: Artificial Sequence
<220> FEATURE:
<223> OTHER INFORMATION: miR-548 variant

<400> SEQUENCE: 55
aaaaguaauc acuguuuuug cc                                              22

<210> SEQ ID NO 56
<211> LENGTH: 23
<212> TYPE: DNA
<213> ORGANISM: Artificial Sequence
<220> FEATURE:
<223> OTHER INFORMATION: miR-548 variant

<400> SEQUENCE: 56
caaaaaccgc aauuacuuuu gca                                             23

<210> SEQ ID NO 57
<211> LENGTH: 25
<212> TYPE: DNA
<213> ORGANISM: Artificial Sequence
<220> FEATURE:
<223> OTHER INFORMATION: miR-548 variant

<400> SEQUENCE: 57
aaaaaccaca auuacuuuug cacca                                           25

<210> SEQ ID NO 58
<211> LENGTH: 25
<212> TYPE: DNA
<213> ORGANISM: Artificial Sequence
<220> FEATURE:
```

<223> OTHER INFORMATION: miR-548 variant

<400> SEQUENCE: 58
aaaaaccaca auuacuuuug cacca                                            25

<210> SEQ ID NO 59
<211> LENGTH: 22
<212> TYPE: DNA
<213> ORGANISM: Artificial Sequence
<220> FEATURE:
<223> OTHER INFORMATION: miR-548 variant

<400> SEQUENCE: 59
ccaaaacugc aguuacuuuu gc                                               22

<210> SEQ ID NO 60
<211> LENGTH: 22
<212> TYPE: DNA
<213> ORGANISM: Artificial Sequence
<220> FEATURE:
<223> OTHER INFORMATION: miR-548 variant

<400> SEQUENCE: 60
aaaaguaauc gcgguuuuug uc                                               22

<210> SEQ ID NO 61
<211> LENGTH: 22
<212> TYPE: DNA
<213> ORGANISM: Artificial Sequence
<220> FEATURE:
<223> OTHER INFORMATION: miR-548 variant

<400> SEQUENCE: 61
aaaaguaauu guggauuuug cu                                               22

<210> SEQ ID NO 62
<211> LENGTH: 22
<212> TYPE: DNA
<213> ORGANISM: Artificial Sequence
<220> FEATURE:
<223> OTHER INFORMATION: miR-548 variant

<400> SEQUENCE: 62
caaaaaccgg caauuacuuu ug                                               22

<210> SEQ ID NO 63
<211> LENGTH: 22
<212> TYPE: DNA
<213> ORGANISM: Artificial Sequence
<220> FEATURE:
<223> OTHER INFORMATION: miR-548 variant

<400> SEQUENCE: 63
gaaaacgaca augacuuuug ca                                               22

<210> SEQ ID NO 64
<211> LENGTH: 21
<212> TYPE: DNA
<213> ORGANISM: Artificial Sequence
<220> FEATURE:
<223> OTHER INFORMATION: miR-548 variant

<400> SEQUENCE: 64
caaaaacugc aauuacuuuc a                                                21

```
<210> SEQ ID NO 65
<211> LENGTH: 21
<212> TYPE: DNA
<213> ORGANISM: Artificial Sequence
<220> FEATURE:
<223> OTHER INFORMATION: miR-548 variant

<400> SEQUENCE: 65
caaaaacugc aauuacuuuc a                                              21

<210> SEQ ID NO 66
<211> LENGTH: 21
<212> TYPE: DNA
<213> ORGANISM: Artificial Sequence
<220> FEATURE:
<223> OTHER INFORMATION: miR-548 variant

<400> SEQUENCE: 66
aaagguaauu gugguuucug c                                              21

<210> SEQ ID NO 67
<211> LENGTH: 21
<212> TYPE: DNA
<213> ORGANISM: Artificial Sequence
<220> FEATURE:
<223> OTHER INFORMATION: miR-548 variant

<400> SEQUENCE: 67
aaagguaauu gugguuucug c                                              21

<210> SEQ ID NO 68
<211> LENGTH: 20
<212> TYPE: DNA
<213> ORGANISM: Artificial Sequence
<220> FEATURE:
<223> OTHER INFORMATION: miR-548 variant

<400> SEQUENCE: 68
aaaagugauu gcaguguuug                                                20

<210> SEQ ID NO 69
<211> LENGTH: 22
<212> TYPE: DNA
<213> ORGANISM: Artificial Sequence
<220> FEATURE:
<223> OTHER INFORMATION: miR-548 variant

<400> SEQUENCE: 69
aaagguaauu gcaguuuuc cc                                              22

<210> SEQ ID NO 70
<211> LENGTH: 21
<212> TYPE: DNA
<213> ORGANISM: Artificial Sequence
<220> FEATURE:
<223> OTHER INFORMATION: miR-548 variant

<400> SEQUENCE: 70
uaaaaacugc aauuacuuuu a                                              21

<210> SEQ ID NO 71
<211> LENGTH: 21
<212> TYPE: DNA
<213> ORGANISM: Artificial Sequence
<220> FEATURE:
<223> OTHER INFORMATION: miR-548 variant
```

```
<400> SEQUENCE: 71
uaaaaacugc aauuacuuuu a                                              21

<210> SEQ ID NO 72
<211> LENGTH: 20
<212> TYPE: DNA
<213> ORGANISM: Artificial Sequence
<220> FEATURE:
<223> OTHER INFORMATION: miR-548 variant

<400> SEQUENCE: 72
uaaaaacugc aauuacuuuc                                                20

<210> SEQ ID NO 73
<211> LENGTH: 21
<212> TYPE: DNA
<213> ORGANISM: Artificial Sequence
<220> FEATURE:
<223> OTHER INFORMATION: miR-548 variant

<400> SEQUENCE: 73
aaaaguaacu gcgguuuuug a                                              21

<210> SEQ ID NO 74
<211> LENGTH: 22
<212> TYPE: DNA
<213> ORGANISM: Artificial Sequence
<220> FEATURE:
<223> OTHER INFORMATION: miR-548 variant

<400> SEQUENCE: 74
aacggcaaug acuuuuguac ca                                             22

<210> SEQ ID NO 75
<211> LENGTH: 22
<212> TYPE: DNA
<213> ORGANISM: Artificial Sequence
<220> FEATURE:
<223> OTHER INFORMATION: miR-548 variant

<400> SEQUENCE: 75
caaaaacugc aguuacuuuu gu                                             22

<210> SEQ ID NO 76
<211> LENGTH: 20
<212> TYPE: DNA
<213> ORGANISM: Artificial Sequence
<220> FEATURE:
<223> OTHER INFORMATION: miR-548 variant

<400> SEQUENCE: 76
aaaaggcauu gugguuuuug                                                20
```

MICRORNA COMPOSITIONS AND METHODS RELATED THERETO

CROSS REFERENCE TO RELATED APPLICATIONS

This application is a PCT Application that claims priority to U.S. Provisional Application No. 61/364,666, filed Jul. 15, 2010, hereby incorporated by this reference.

FIELD

The present disclosure relates generally to the field of molecular biology. It provides compositions and methods involving microRNAs (miRNAs) for the treatment of disorders that can be ameliorated by such miRNAs, particularly neoplasias.

BACKGROUND

Cancer remains one of the most prolific killers in industrialized countries. While surgery, radiation and chemotherapy are effective in the treatment of some cancers, many others are resistant to such therapies. This is evidenced by the high mortality rate; approximately 1 in 4 deaths in the United States are cancer-related. Lung and stomach cancer are particularly deadly, with survival rates averaging 15% after five years. High mortality rates are due in part to their resistance to treatment methods; for example, both stomach and lung cancers are largely insusceptible to chemotherapy treatment. Thus, there is a constant need to develop improved cancer therapies.

In 2001, several groups used a cloning method to isolate and identify a large group of "microRNAs" (miRNAs) from *C. elegans, Drosophila*, and humans (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

MiRNAs thus far observed have been approximately 21-23 nucleotides in length and they arise from longer precursors, which are transcribed from non-protein-encoding genes (Carrington et al., 2003). The precursors form structures that fold back on each other in self-complementary regions; they are then processed by the nuclease Dicer in animals or DCL1 in plants. MiRNA molecules interrupt translation through precise or imprecise base-pairing with their targets.

MiRNAs are involved in gene regulation. Some miRNAs, including lin-4 and let-7, inhibit protein synthesis by binding to partially complementary 3' untranslated regions (UTRs) of target mRNAs. Others, including the Scarecrow miRNA found in plants, function like siRNA and bind to perfectly complementary mRNA sequences to destroy the target transcript (Grishok et al., 2001).

Research on miRNAs is increasing as scientists are beginning to appreciate the broad role that these molecules play in the regulation of eukaryotic gene expression. The two best understood miRNAs, lin-4 and let-7, regulate developmental timing in *C. elegans* by regulating the translation of a family of key mRNAs (Pasquinelli, 2002). Several hundred miRNAs have been identified in *C. elegans, Drosophila* and mouse. More than thousand miRNAs have been discovered in humans. As would be expected for molecules that regulate gene expression, miRNA levels have been shown to vary between tissues and developmental states.

MicroRNAs and Cancer

There is growing realization that miRNAs, in addition to functioning as regulators of development, can act as oncogenes and tumor suppressors (Akao et al., 2006; Esquela-Kerscher and Slack, 2006; He et al., 2005). Data suggests the dysregulation of miRNA expression in cancer cells (Cho, 2009; Galasso et al., 2010; Garzon et al, 2006; Leite et al., 2009; Li et al., 2010; Ohlsson Teague et al., 2009; Tie et al., 2010; Varnholt et al., 2008). Moreover, altered expression of specific miRNAs has been demonstrated to promote tumorigenesis. Thus, these miRNA expression changes are informative for cancer classification and prognosis.

Events leading to the development of cancer from normal tissue have been well characterized, and a necessary step in this process is the dysregulation of cell cycle progression that facilitates the propagation and accumulation of genetic mutations. Within each cell, elaborate machinery exists to halt cell cycle progression in response to various stimuli, including DNA damage. Such regulation provides time for DNA repair prior to its replication and cell division, hence preserving the integrity of the genome. Multiple pathways lead to cell cycle arrest; however, the p53 tumor suppressor pathway has been shown to lead to both $G_1$ and $G_2M$ arrest (Vousden et al., 2007; Taylor et al., 2001; Brown et al., 2007). Although a number of players in this pathway have been identified and characterized, the precise mechanism by which DNA damage leads to cell cycle arrest remains only partially understood.

Cell cycle arrest in response to DNA damage is an important anti-tumorigenic mechanism. MiRNAs have been shown to play regulatory roles in cell cycle progression. In doing so, miRNAs regulate biological processes including cell growth, differentiation and death (Bartel et al., 2004). Insight has been gained into the miRNA-mediated cell cycle regulation by identifying target transcripts of respective miRNAs (Carleton, 2007; Johnson et al., 2007; Ivanovsaka, I., et al., 2008). For example, miR-34a is induced in response to p53 activation and mediates $G_1$ arrest by down-regulating multiple cell cycle-related transcripts.

While certain miRNAs exert their cell cycle effect through targeting transcripts, other miRNAs do so through cooperatively down-regulating the expression of multiple cell cycle-related transcripts (He et al., 2007; Linsley et al., 2007). In addition to their effects on the cell cycle, these miRNAs and their family members are aberrantly expressed in human cancers (Linsley et al., 2007; Calin et al., 2006; Takamizawa et al., 2004; Inamura et al., 2007; Cimminio et al., 2005; Ota et al., 2004; He et al., 2005).

Cancer causes one in every four US deaths and is the first leading cause of death among Americans. Despite extensive research into the development of therapies, current neoplasia treatments are woefully ineffective. Many mechanisms of miRNA regulation, including their targets and roles in neoplastic transformations, have not yet been investigated. Thus, there is an unfulfilled need for improved compositions and methods for the treatment or prevention of neoplasia.

SUMMARY

The present disclosure is based on the identification of microRNA (miRNA) located within the fourth intron of the human fragile histidine triad (FHIT) gene. The present disclosure provides evidence that 1) certain miRNA (e.g. "miR2") is dysregulated in human and cancer cell lines; 2) certain miRNA shows strong effects on inhibiting human tumors in a xenograft mouse model; and 3) certain Cyclin D1 and Her2, two important oncogenes in human cancer development, are targets of the miRNA; 4) the miRNA belongs to the miR-548 family that is a unique group of miRNAs only known to exist in chimps and humans, and is associated with the chromosome fragile sites. The miRNA with the other members of the miR-548 family share conserved seed sequence, indicating that the miR-548 family is a group unique tumor suppressor.

It is believed that nucleic acid sequence of miR2 that target Cyclin D1 (AAAAG(C)U—(SEQ ID NO: 10) and UUUUGU (C)—(SEQ ID NO:11)) is relatively conserved in the miR-548 family. Therefore, anti-human tumor growth of the miR-548 family is included in this disclosure. MiR-548 family of sequences include mature sequences selected from:

| Sequence | ID |
|---|---|
| CAAAACUGGCAAUUACUUUUGC, | (SEQ ID NO: 18) |
| AAAAGUAAUUGUGGUUUUGGCC, | (SEQ ID NO: 19) |
| CAAAACUGGCAAUUACUUUUGC, | (SEQ ID NO: 20) |
| AAAAGUAAUUGCGAGUUUUACC, | (SEQ ID NO: 21) |
| AAAAGUAAUUGCGGUUUUUGCC, | (SEQ ID NO: 22) |
| AAAAGUAAUUGUGGUUUUUGCC, | (SEQ ID NO: 23) |
| AAAAGUAAUUGUGGUUUUUGCC, | (SEQ ID NO: 24) |
| AAAAACUGAGACUACUUUUGCA, | (SEQ ID NO: 25) |
| AAAAGUAAUUGCGUCUUUGGU, | (SEQ ID NO: 26) |
| AAAAGUACUUGCGGAUUUUGCU, | (SEQ ID NO: 27) |
| AAAAGUAUUUGCGGGUUUUGUC, | (SEQ ID NO: 28) |
| AAAAACUGUAAUUACUUUU, | (SEQ ID NO: 29) |
| AAAAACUGUAAUUACUUUU, | (SEQ ID NO: 30) |
| AAAAACUGUAAUUACUUUU, | (SEQ ID NO: 31) |
| AAAAACUGUAAUUACUUUU, | (SEQ ID NO: 32) |
| AAAAACUGUAAUUACUUUU, | (SEQ ID NO: 33) |
| AAAACUGUAAUUACUUUUGUAC, | (SEQ ID NO: 34) |
| CAAAAGUAAUUGUGGAUUUUGU, | (SEQ ID NO: 35) |
| CAAAGGUAUUGUGGUUUUUG, | (SEQ ID NO: 36) |
| CCAAAACUGCAGUUACUUUUGC, | (SEQ ID NO: 37) |
| AAAAGUAAUCGCGGUUUUUGUC, | (SEQ ID NO: 38) |
| AAAAGUAAUCGCGGUUUUUGUC, | (SEQ ID NO: 39) |
| AAAAGUAAUCGCGGUUUUUGUC, | (SEQ ID NO: 40) |
| AAAAGUAAUCGCGGUUUUUGUC, | (SEQ ID NO: 41) |
| UAGCAAAAACUGCAGUUACUUU, | (SEQ ID NO: 42) |
| AAAAGUAAUUGCGGAUUUUGCC, | (SEQ ID NO: 44) |
| AAAAGUAAUUGCGGAUUUUGCC, | (SEQ ID NO: 45) |
| AAAAGUAAUUGCGGAUUUUGCC, | (SEQ ID NO: 46) |
| AAAAGUAAUUGCGGAUUUUGCC, | (SEQ ID NO: 47) |
| GCUGGUGCAAAAGUAAUGGCGG, | (SEQ ID NO: 48) |
| AUGGCCAAAACUGCAGUUAUUUU, | (SEQ ID NO: 49) |
| CAAAAGUGAUCUGGGUUUUUG, | (SEQ ID NO: 50) |
| CAAAGACUGCAAUUACUUUUGCG, | (SEQ ID NO: 51) |
| AGCUACAGUUACUUUUGCACCA, | (SEQ ID NO: 52) |
| AAAAGUAACUGCGGUUUUUGCCU, | (SEQ ID NO: 53) |
| UAAAAACUGCAAUUACUUUC, | (SEQ ID NO: 54) |
| AAAAGUAAUCACUGUUUUUGCC, | (SEQ ID NO: 55) |
| CAAAAACCGCAAUUACUUUUGCA, | (SEQ ID NO: 56) |
| AAAAACCACAAUUACUUUUGCACCA, | (SEQ ID NO: 57) |
| AAAAACCACAAUUACUUUUGCACCA, | (SEQ ID NO: 58) |
| CCAAAACUGCAGUUACUUUUGC, | (SEQ ID NO: 59) |
| AAAAGUAAUCGCGGUUUUUGUC, | (SEQ ID NO: 60) |
| AAAAGUAAUUGUGGAUUUUGCU, | (SEQ ID NO: 61) |
| CAAAAACCGGCAAUUACUUUUG, | (SEQ ID NO: 62) |
| GAAAACGACAAUGACUUUUGCA, | (SEQ ID NO: 63) |
| CAAAAACUGCAAUUACUUUCA, | (SEQ ID NO: 64) |
| CAAAAACUGCAAUUACUUUCA, | (SEQ ID NO: 65) |
| AAAGGUAAUUGUGGUUUCUGC, | (SEQ ID NO: 66) |
| AAAGGUAAUUGUGGUUUCUGC, | (SEQ ID NO: 67) |
| AAAAGUGAUUGCAGUGUUUG, | (SEQ ID NO: 68) |
| AAAAGGUAAUUGCAGUUUUUCCC, | (SEQ ID NO: 69) |
| UAAAAACUGCAAUUACUUUUA, | (SEQ ID NO: 70) |
| UAAAAACUGCAAUUACUUUUA, | (SEQ ID NO: 71) |
| UAAAAACUGCAAUUACUUUC, | (SEQ ID NO: 72) |
| AAAAGUAACUGCGGUUUUUGA, | (SEQ ID NO: 73) |
| AACGGCAAUGACUUUUGUACCA, | (SEQ ID NO: 74) |
| CAAAAACUGCAGUUACUUUUGU, and | (SEQ ID NO: 75) |
| AAAAGGCAUUGUGGUUUUUG. | (SEQ ID NO: 76) |

The present disclosure provides compositions featuring microRNA and its method of use in the treatment of neoplasias. In certain embodiments, the disclosure relates to isolated nucleic acid molecules comprising miR2 nucleotide sequence such as a nucleotide sequence comprising SEQ ID NO: 1-76. The nucleic acid may be less than 500, 400, 300, 100, 50, 40, 30, 25, or 20 nucleotides or base pairs. Sometimes the nucleic acid molecule consisting essentially of a nucleotide sequence comprising SEQ ID NOs:1-76. The nucleotide sequence may be a recombinant vector in operable combination with a promoter region, a start codon, and expressed in a host cell or other non-cellular expression system.

In certain embodiments, the disclosure relates to nucleic acid sequences, compositions, and methods disclosed herein which contain nucleic acid sequences comprising a first nucleotide sequence AAA (SEQ ID NO:6) or AAAX (SEQ ID NO:7) or wherein X is G or C, and a second nucleotide sequence UUU (SEQ ID NO:8) or UUUG (SEQ ID NO:9), provided that any U individually and independently may be uracil or thymine. The nucleic acid may be less than 500, 400, 300, 100, 50, 40, 30, 25, 24, 23, 22, 21, 20, 19, 18, 17, 16, or 15 nucleotides or base pairs wherein the first and the second sequences are separated by 8, 9, 10, 11, 12 nucleotides of any sequence. In some embodiments, the first nucleotide sequence is SEQ ID NO:6 and the second nucleotide sequence is SEQ ID NO:8. In some embodiments, the first nucleotide sequence is SEQ ID NO:6 and the second nucleotide sequence is SEQ ID NO:9. In some embodiments, the first nucleotide sequence is SEQ ID NO:7 and the second nucleotide sequence is SEQ ID NO:8. In some embodiments, the first nucleotide sequence is SEQ ID NO:7 and the second nucleotide sequence is SEQ ID NO:9.

In certain embodiments, the disclosure relates to nucleic acid sequences, compositions, and methods disclosed herein which contain nucleic acid sequences comprising a first nucleotide sequence AAAXU (SEQ ID NO:12) or AAAXT (SEQ ID NO:13), wherein X is G or C, and a second nucleotide sequence UUUGY (SEQ ID NO:14), wherein Y is U or C, provided that any U individually and independently may be uracil or thymine. The nucleic acid may be less than 500, 400, 300, 100, 50, 40, 30, 25, 24, 23, 22, 21, 20, 19, 18, 17, 16, or 15 nucleotides or base pairs.

In certain embodiments, the disclosure relates to nucleic acid sequences, compositions, and methods disclosed herein which contain nucleic acid sequences comprising a first nucleotide sequence AAAAXU (SEQ ID NO:15) or AAAAXT (SEQ ID NO:16), wherein X is G or C, and a second nucleotide sequence UUUUGY (SEQ ID NO:17), wherein Y is U or C, provided that any U individually and independently may be uracil or thymine. The nucleic acid may be less than 500, 400, 300, 100, 50, 40, 30, 25, 24, 23, 22, 21, 20, 19, 18, 17, 16, or 15 nucleotides or base pairs.

In one aspect, the disclosure features a substantially purified nucleic acid molecule containing a nucleotide sequence having at least 90%, 95%, 97%, 99% or 100% identity to the sequence of a microRNA that is miR2, a fragment thereof, or any combination thereof and the miR-548 family. In one embodiment, the purified nucleic acid molecule contains a nucleotide sequence having at least 90%, 95%, 97%, 99% or 100% identity to the sequence of a microRNA that is miR2, a fragment thereof, or any combination thereof and a pharmaceutically acceptable carrier and the miR-548 family. In another embodiment, the purified nucleic acid molecule contains a modified nucleotide sequence having at least 90%, 95%, 97%, 99% or 100% identity to the sequence of a microRNA that is miR2 that is modified to increase its bioavailability, a fragment thereof, or any combination thereof and a pharmaceutically acceptable carrier and the miR-548 family. In a related aspect, the disclosure features a recombinant vector encoding a nucleic acid molecule containing a nucleotide base sequence having at least 90%, 95%, 97%, 99% or 100% identity to the sequence of a microRNA that is miR2, a fragment thereof, or any combination thereof and the miR-548 family, where the nucleic acid molecules is/are positioned for expression in a mammalian cell. In one embodiment, the vector is a viral vector selected from the group consisting of a retroviral, adenoviral, lentiviral or adeno-associated viral vector. In another embodiment, the viral vector is capable of targeting cells of the central nervous system.

In a related aspect, the disclosure features a host cell (e.g., a human cell, such as a neoplastic cell) containing the expression vector of a previous aspect or a nucleic acid molecule delineated herein. In another aspect, the disclosure features a pharmaceutical composition for the treatment of a neoplastic cell, the composition containing an oligonucleotide having at least 90%, 95%, 97%, 99% or 100% identity to the sequence of a microRNA that is miR2 and the miR-548 family, any fragment thereof, or any combination thereof, and a pharmaceutically acceptable excipient. In one embodiment, the amount of microRNA is sufficient to reduce the survival or proliferation of a neoplastic cell by at least about 5%, 10%, 25%, 50%, 75%, or 100% relative to an untreated control cell.

In another aspect, the disclosure features a pharmaceutical composition for the treatment of a neoplasia, the composition containing an effective amount of an expression vector encoding a microRNA that contains miR2 and a pharmaceutically acceptable excipient. In one embodiment, the amount of microRNA is sufficient to reduce the survival or proliferation of a neoplastic cell by at least about 5%, 10%, 25%, 50%, 75%, or 100% relative to an untreated control cell.

In another aspect, the disclosure provides a method of reducing the growth, survival or proliferation of a neoplastic cell, the method involving contacting the cell with an oligonucleotide containing a nucleotide sequence having at least 90%, 95%, 97%, 99% or 100% identity to miR2 and the miR-548 family.

In another aspect, the disclosure features a method of reducing the growth, survival or proliferation of a neoplastic cell, the method involving contacting the cell with an expression vector encoding a microRNA that contains miR2, or any fragment or combination thereof and the miR-548 family, thereby reducing the growth, survival or proliferation of a neoplastic cell relative to an untreated control cell.

In another aspect, the disclosure features a method of treating a neoplasia in a subject (e.g., a human or veterinary patient), the method involving administering to the subject an effective amount of an oligonucleotide containing a nucleotide sequence having at least 90%, 95%, 97%, 99% or 100% identity to miR2 and the miR-548 family.

In addition, methods of the disclosure concern employing an oligonucleotide containing the miR2 sequence and an additional therapeutic agent such as the miR-548 family. The nucleic acid can enhance the effect or efficacy of the agent, reduce any side effects or toxicity, modify its bioavailability, decrease the dosage or frequency needed, and/or increase apoptosis. In certain embodiments, the therapeutic agent is a cancer therapeutic. Consequently, in some embodiments, there is a method of treating neoplasia in a patient comprising administering to the patient a cancer therapeutic and miR2 and the miR-548 family.

In one aspect, there is provided a method of treating a neoplasia in an individual comprising a) a first therapy comprising administering to the individual a composition comprising miR2, and b) a second therapy comprising radiation therapy, surgery, or combinations thereof. In some variations, the second therapy is radiation therapy. In some variations, the second therapy is surgery. In some variations, the first therapy is carried out prior to the second therapy. In some variations, the first therapy is carried out after the second therapy.

In another aspect, the method comprises administering to a mammal having a neoplasia a combination therapy comprising a first therapy comprising a composition of miR2 or any combination thereof including the miR-548 family and a second therapy selected from the group consisting of chemotherapeutic agent and radiation or combinations thereof. The combination therapy may be administered in any of a variety of ways such as sequentially or simultaneously, and if sequential, miR2 and the miR-548 family may be administered before or after the second therapy. It will also be understood that the second therapy can include more than one chemotherapeutic agent.

In other embodiments of the disclosure, there are methods of increasing the percentage of apoptotic cells in a population comprising introducing into or providing to the cells a miRNA molecule that corresponds to a miRNA sequence. In certain embodiments the methods involve providing to or introducing into cells an effective amount of one or more nucleic acid molecules capable of being processed into a mature miRNA when it is inside the cell, wherein the mature miRNA is miR2 and the miR-548 family. It is specifically contemplated that the population of cells may be neoplastic or related to a neoplastic condition.

In various embodiments of any of the above aspects, the neoplasia is of the stomach. In yet other embodiments, it is of the lung. In yet other embodiments, it is of the cervix.

In various embodiments of any of the above aspects, the chemotherapy treatment is composed of one or more DNA-damaging agents. In yet other embodiments, the DNA-damaging agents induce double strand breaks in DNA. In yet other embodiments, the DNA-damaging agents inhibit topoisomerases. Examples of DNA damaging agents, include, but are not limited to adriamycin, anthracycline, bleomycin, etoposide, or 5-fluorouracil, irinotecan, radiation therapy, mitoxantrone, or any derivative, analog, or combination thereof.

In other embodiments, the oligonucleotide(s) contains at least one modified linkage (e.g., phosphorothioate, methylphosphonate, phosphotriester, phosphorodithioate, and phosphoselenate linkages), contains at least one modified sugar moiety or one modified nucleotide.

In various embodiments of the above aspects, the neoplasia expresses miR2 and the miR-548 family by at least 1%, 5%, 10%, 25%, 50%, 75%, 90%, or 100% above or below baseline levels.

In various embodiments of the above aspects, the composition or methods increase the expression level of miR2 and the miR-548 family by at least 1%, 5%, 10%, 25%, 50%, 75%, 90%, or 100% above baseline levels.

In various embodiments of any of the above aspects, the compositions or methods reduce the growth, survival, or proliferation of a neoplastic cell relative to an untreated control cell, or increase the survival rate or prognosis of the affected subject.

It is specifically contemplated that any embodiments described in the Examples section are included as an embodiment of the disclosure.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

DETAILED DESCRIPTION

I. Definitions

Figure 1:
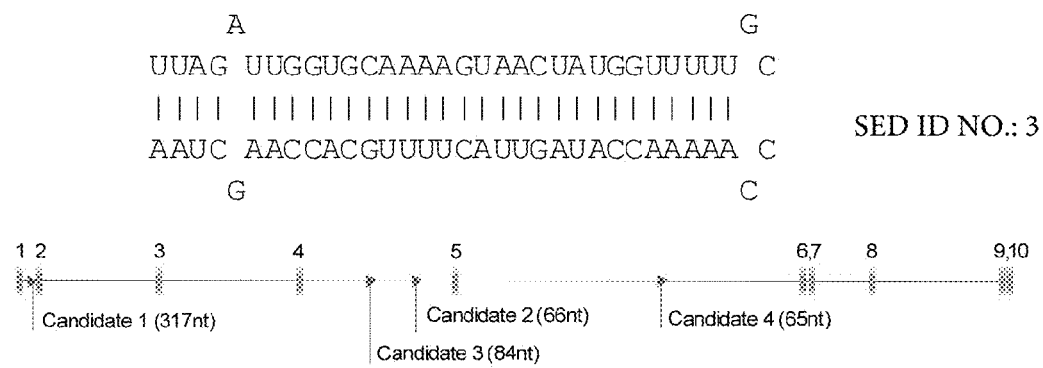
FIG. 1 Prediction of the miR2 location. miR2, the second candidate predicted in Chromosome 3, minus strand, 60,578,579-60,578,644 (SEQ ID NO.: 3) and it is located in the FHIT intron.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The sequence of microRNAs referred to herein is known in the art. In particular, the sequence of microRNAs is publically available via miRBase (http://microrna.sanger.ac.uk/), which provides microRNA data. Each entry in the miRBase Sequence database represents a predicted hairpin portion of a miRNA transcript, with information on the location and sequence of the mature miRNA sequence. Both hairpin and mature sequences are available for searching using BLAST and SSEARCH, and entries can also be retrieved by name, keyword, references and annotation.

The term "purified" does not require absolute purity or isolation; rather, it is intended as a relative term. Thus, for example, a purified (or isolated) nucleic acid preparation is one in which the nucleic acid is more pure than the nucleic acid in its natural environment within a cell. Such nucleic acids may be produced, for example, by standard purification techniques, or by recombinant expression. In some embodiments, a preparation of a nucleic acid is purified such that the nucleic acid represents at least 50%, for example at least 70%, of the total nucleic acid content of the preparation.

An isolated biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins that have been isolated include nucleic acids and proteins purified by standard purification methods. The term also embraces nucleic acids, peptides, and proteins prepared by recombinant expression in a host cell as well as chemically synthesized nucleic acids. A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al. (In: Molecular Cloning: A Laboratory Manual, Cold Spring Harbor, N.Y., 1989).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. A nucleic acid is also contemplated to include locked nucleic acid (LNA), a modified RNA. The ribose moiety of an LNA nucleotide is modified with an extra bridge connecting the 2' oxygen and 4' carbon. The bridge "locks" the ribose in the 3'-endo conformation, which is often found in the A-form duplexes. LNA nucleotides can be mixed with DNA or RNA residues in the oligonucleotide whenever desired. Such oligomers are synthesized chemically and are commercially available. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of the disclosure may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., Molecular Cloning: A Laboratory Manual. 3rd ed., Cold Spring Harbor Press, Cold Spring Harbor, N.Y., 2001; and Ausubel et al., Current Protocols in Molecular Biology. Greene Publishing Associates and John Wiley & Sons, NY, 1994. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine-substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminonoethyl-2-thiouridine, 5 -carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, Nθ-substituted adenine, 7-methylguanine, 5-methylaminomethyluracil, 5-methoxyaminomethyl- 2-thiouracil, beta-D-mannosylqueosine, 5-methoxycarboxymethyluracil, 5-methoxyuracil, 2- methylthio-N6-isopentenyladenine, uracil- 5-oxyacetic acid (v), wybutoxosine, pseudouracil, queosine, 2-thiocytosine, 5-methyl-2- thiouracil, 2-thiouracil, 4-thiouracil, 5-methyluracil, uracil- 5-oxyacetic acid methylester, 3-(3-amino-3-N-2-carboxypropyl)uracil, and 2,6-diaminopurine. Alternatively, one or more of the nucleic acids of the disclosure can be purchased from companies, such as Macromolecular Resources (Fort Collins, Colo.) and Synthegen (Houston, Tex.).

It will be understood that shorthand notations are employed such that a generic description of a miRNA refers to any of its gene family members (distinguished by a number), unless otherwise indicated. It is understood by those of skill in the art that a "gene family" refers to a group of genes having the same miRNA coding sequence. Typically, a number following the initial designation identifies members of a gene family.

The term "miR2" refers to the nucleic acid sequence TTA-GATTGGTGCA AAAGTAACTATGGTTTTTGC-CCAAAAACCATAGTTACTTTTGCACCAAGCTAA (hairpin) (SEQ ID NO:1), or phosphate linkage, sugar, or base modifications or fragments greater than 10, 12, 14, 16, 18, 20, or 22 nucleotides thereof such as AAAAGTAACTATG-GTTTTTGC (mature) (SEQ ID NO:2) or similar sequence (e.g., with a sequence identity of greater than 70%, 80%, 90%, 95%, or 98%). It is contemplated to include harpin, double stranded, and single stranded versions. It is contemplated to include both RNA and DNA. In certain embodiments, the disclosure contemplates sequences above wherein all thymine may be uracil such as UUAGAUUGGUGCA AAAGUAACUAUGGUUUUUGCCCAAAAAC-CAUAGUUACUUUUGCACCAAGCUAA (SEQ ID NO:3) AAAAGUAACUAUGGUUUUUGC (SEQ ID NO:4) Cytosine may be methylated to unmethylated. It is contemplated that the nucleic acid may be linked to polyethylene glycol, acyl, or hydrocarbon groups to facilitate solubility and improve stability.

By "miR2 gene" is meant a polynucleotide that encodes a miR2 microRNA or analog thereof.

By "alteration" is meant a change (increase or decrease) in the expression levels of a gene or polypeptide as detected by standard art known methods such as those described above. As used herein, an alteration includes a 5% change in expression levels, preferably a 25% change, more preferably a 40% change, and most preferably a 50% or greater change in expression levels.

In this disclosure, "comprises," "comprising," "containing" and "having" and the like can have the meaning ascribed to them in U.S. Patent law and can mean " includes," "including," and the like; "consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference condition. By "an effective amount" is meant the amount of an agent required to ameliorate the symptoms of a disease relative to an untreated patient. The effective amount of active agent(s) used to practice the present disclosure for therapeutic treatment of a neoplasia varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference protein or nucleic acid.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "inhibits a neoplasia" or "inhibits a neoplasia of the central nervous system" is meant decreases the propensity of a cell to develop into a neoplasia of the central nervous system or slows, decreases, or stabilizes the growth or proliferation of a neoplasia of the central nervous system.

By "isolated nucleic acid molecule" is meant a nucleic acid (e.g., a DNA, RNA, microRNA or analog thereof) that is free of the genes which, in the naturally-occurring genome of the organism from which the nucleic acid molecule of the disclosure is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes a microRNA or other RNA molecule which is transcribed from a DNA molecule, as well as a recombinant DNA which is part of a hybrid gene encoding additional polypeptide sequence.

By "marker" is meant any protein or polynucleotide having an alteration in expression level or activity that is associated with a disease or disorder.

By "modification" is meant any biochemical or other synthetic alteration of a nucleotide, amino acid, or other agent relative to a naturally occurring reference agent.

By "neoplasia" is meant any disease that is caused by or results in inappropriately high levels of cell division, inappropriately low levels of apoptosis, or both. For example, cancer is a neoplasia. Examples of cancers include, without limitation, leukemias (e.g., acute leukemia, acute lymphocytic leukemia, acute myelocytic leukemia, acute myeloblasts leukemia, acute promyelocyte leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, stomach cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "mature form" is meant a microRNA that has, at least in part, been processed into a biologically active form that can participate in the regulation of a target mRNA.

By "hairpin form" is meant a microRNA that includes a double stranded portion. By "microRNA" is meant a nucleotide sequence having biological activity that is independent of any polypeptide encoding activity. MicroRNAs may be synthetic or naturally occurring, and may include one or more modifications described herein. MicroRNAs include pri-microRNAs, hairpin microRNAs, and mature microRNAs.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

By "obtaining" as in "obtaining the inhibitory nucleic acid molecule" is meant synthesizing, purchasing, or otherwise acquiring the inhibitory nucleic acid molecule.

By "oligonucleotide" is meant any molecule comprising a nucleotide sequence. An oligonucleotide may, for example, include one or more modified bases, linkages, sugar moieties, or other modifications.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 6, 7, 8, 9, 10, 11, 12, 13, 14, 15, 16, 17, 18, 19, 20, or 21 nucleotides.

By "reduces" is meant a negative alteration. A reduction includes, for example, a 1%, 5%, 10%, 25%, 50%, 75%, 90%, or even 100% reduction. By "reduces the survival" is meant increases the probability of cell death in a cell or population of cells relative to a reference. For example, a reduction in survival is measured in a cell treated with a microRNA of the disclosure relative to an untreated control cell. Cell death may be by any means, including apoptotic or necrotic cell death.

"Radiation therapy" (also called "radiotherapy", "x-ray therapy", or "irradiation") is the use of a certain type of energy (called ionizing radiation) to kill cancer cells and shrink tumors. Radiation therapy injures or destroys cells in the area being treated (the "target tissue") by damaging their genetic material, making it impossible for these cells to continue to grow and divide. Although radiation damages both cancer cells and normal cells, most normal cells can recover from the effects of radiation and function properly. The goal of radiation therapy is to damage as many cancer cells as possible, while limiting harm to nearby healthy tissue. There are different types of radiation and different ways to deliver the radiation. For example, certain types of radiation can penetrate more deeply into the body than can others. In addition, some types of radiation can be very finely controlled to treat only a small area (an inch of tissue, for example) without damaging nearby tissues and organs. Other types of radiation are better for treating larger areas. In some cases, the goal of radiation treatment is the complete destruction of an entire tumor. In other cases, the aim is to shrink a tumor and relieve symptoms. This type of therapy includes without limitation external-beam therapy, internal radiation therapy, implant radiation, brachytherapy, systemic radiation therapy, and radiotherapy.

"Chemotherapy" means the administration of one or more anti-cancer drugs such as, antineoplastic chemotherapeutic agents, chemopreventative agents, and/or other agents to a cancer patient by various methods, including intravenous, oral, intramuscular, intraperitoneal, intravesical, subcutaneous, transdermal, buccal, or inhalation or in the form of a suppository. Chemotherapy may be given prior to surgery to shrink a large tumor prior to a surgical procedure to remove it, after surgery or radiation therapy to prevent the growth of any remaining cancer cells in the body.

The term "topoisomerase" refers to any enzyme that unwinds and/or winds DNA, in order for DNA to control the synthesis of proteins, and to facilitate DNA replication. The enzyme is necessary due to inherent problems caused by the DNA's double helix. In order to help overcome these problems caused by the double helix, topoisomerases bind to either single-stranded or double stranded DNA and cut the phosphate backbone of the DNA. This intermediate break allows the DNA to be untangled or unwound, and at the end of these processes, the DNA is reconnected again.

The term "topoisomerase inhibitor" refers to any substance that inhibits the activity of topisomerase by 1%, 5%, 10%, 25%, 50%, 75%, 90%, or 100%, measured in any cell, tissue, or extract, relative to untreated control samples.

By "reduces cell division" is meant interferes with the cell cycle or otherwise reduces the growth or proliferation of a cell, tissue, or organ relative to a reference. For example, a reduction in cell division is measured in a cell treated with a microRNA of the disclosure relative to an untreated control cell.

The term "subject" is intended to include vertebrates, preferably a mammal. Mammals include, but are not limited to, humans.

The term "pharmaceutically-acceptable excipient" as used herein means one or more compatible solid or liquid filler, diluents or encapsulating substances that are suitable for administration into a human.

By "transformed cell" is meant a cell into which (or into an ancestor of which) has been introduced, by means of recombinant DNA techniques, a polynucleotide molecule encoding (as used herein) a protein of the disclosure.

The nucleic acids of the disclosure can be incorporated into a recombinant expression vector. In this regard, the disclosure provides recombinant expression vectors comprising any of the nucleic acids of the disclosure. For purposes herein, the term "recombinant expression vector" or "vector" means a genetically-modified oligonucleotide or polynucleotide construct that permits the expression of an RNA, protein, polypeptide, or peptide by a host cell, when the construct comprises a nucleotide sequence encoding the RNA, protein, polypeptide, or peptide, and the vector is contacted with the cell under conditions sufficient to have the RNA, protein, polypeptide, or peptide expressed within the cell. The vectors of the disclosure are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the disclosure can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Burlington, Ontario), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGT1 1, λZapII (Stratagene, La Jolla, Calif.), λEMBL4, and λNM1 149, also can be used. Examples of plant expression vectors include pBIO1, pBI101.2, pBI101.3, pBI121 and pBIN19 (Clontech, Palo Alto, Calif.). Examples of animal expression vectors include pEUK-C1, pMAM and pMAMneo (Clontech, Palo Alto, Calif.). Preferably, the recombinant expression vector is a viral vector, e.g., a retroviral vector.

The recombinant expression vectors of the disclosure can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. [0065] Replication systems can be derived, e.g., from CoIE1, 2 μ plasmid, λ, S V40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the miR2, and/or mimics thereof (including functional portions and functional variants thereof), or to the nucleotide sequence which is complementary to or which hybridizes to the nucleotide sequence encoding the RNA. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an S V40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

In one embodiment, nucleic acid molecules useful in the methods of the disclosure include any nucleic acid molecule that encodes a polynucleotide (e.g., a microRNA) that has biologic activity independent of providing a polypeptide sequence. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 ° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

II. MicroRNAs

MicroRNAs are small non-coding RNA molecules that are capable of causing post-transcriptional silencing of specific genes in cells by the inhibition of translation or through degradation of the targeted mRNA. A microRNA can be completely complementary or can have a region of non-complementarity with a target nucleic acid, consequently resulting in a "bulge" at the region of non-complementarity. A microRNA can inhibit gene expression by repressing translation, such as when the microRNA is not completely complementary to the target nucleic acid, or by causing target RNA degradation, which is believed to occur only when the microRNA binds its target with perfect complementarity. The disclosure also can include double-stranded precursors of microRNA. A microRNA or pri- microRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors typically have a length of about 70-100 nucleotides and have a hairpin conformation. MicroRNAs are generated in vivo from premiRNAs by the enzymes Dicer and Drosha, which specifically process long pre-miRNA into functional miRNA. The hairpin or mature microRNAs, or pri-microRNA agents featured in the disclosure can be synthesized in vivo by a cell-based system or in vitro by chemical synthesis.

In various embodiments of the above disclosure, the oligonucleotide contains the nucleotide sequence of the miR2 microRNA. In another embodiment, the oligonucleotide consists essentially of the nucleotide sequence of the miR2 microRNA. In yet other embodiments, the miR2microRNA sequence is a pre-microRNA, mature or hairpin form.

In other embodiments, a combination of oligonucleotides containing essentially the sequences of miR2, any pre-miRNA, any fragment, or any combination thereof is envisioned.

The disclosure provides isolated microRNAs and polynucleotides encoding such sequences. A recombinant microRNA of the disclosure (e.g., miR2) or a polynucleotide encoding such a microRNA may be administered to reduce the growth, survival, or proliferation of a neoplastic cell in a subject in need thereof In one approach, the microRNA is administered as a naked RNA molecule. In another approach, it is administered in an expression vector suitable for expression in a mammalian cell.

One exemplary approach provided by the disclosure involves administration of a recombinant therapeutic, such as a recombinant microRNA molecule, variant, or fragment thereof, either directly to the site of a potential or actual disease-affected tissue or systemically (for example, by any conventional recombinant administration technique). The dosage of the administered microRNA depends on a number of factors, including the size and health of the individual patient. For any particular subject, the specific dosage regimes should be adjusted over time according to the individual need and the professional judgment of the person administering or supervising the administration of the compositions.

For example, a microRNA of the disclosure (e.g., miR2) may be administered in dosages between about 1 and 100 mg/kg (e.g., 1, 5, 10, 20, 25, 50, 75, and 100 mg/kg). In other embodiments, the dosage ranges from between about 25 and 500 mg/m^/day. Desirably, a human patient having a neoplasia receives a dosage between about 50 and 300 mg/m^/day (e.g., 50, 75, 100, 125, 150, 175, 200, 250, 275, and 300).

MicroRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism.

Modifications can also increase sequence specificity, and consequently decrease off-site targeting. Methods of synthesis and chemical modifications are described in greater detail below.

If desired, microRNA molecules may be modified to stabilize the microRNAs against degradation, to enhance half-life, or to otherwise improve efficacy. Desirable modifications are described, for example, in U.S. Patent Publication Nos. 20070213292, 20060287260, 20060035254. 20060008822. and 20050288244. each of which is hereby incorporated by reference in its entirety. For increased nuclease resistance and/or binding affinity to the target, the single-stranded oligonucleotide agents featured in the disclosure can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleotide modifications can also increase binding affinity to the target. The inclusion of pyranose sugars in the oligonucleotide backbone can also decrease endonucleolytic cleavage. An antagomir can be further modified by including a 3' cationic group, or by inverting the nucleoside at the 3'-terminus with a 3'-3' linkage. In another alternative, the 3'-terminus can be blocked with an aminoalkyl group. Other 3' conjugates can inhibit 3'-5' exonucleolytic cleavage. While not being bound by theory, a 3' may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the microRNA includes a 2'-modified oligonucleotide containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present disclosure may be used in conjunction with any technologies that may be developed to enhance the stability or efficacy of an inhibitory nucleic acid molecule.

MicroRNA molecules include nucleotide oligomers containing modified backbones or non-natural internucleoside linkages. Oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleotide oligomers. Nucleotide oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest- ers, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleotide oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyl eneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141 ; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. Nucleotide oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleotide oligomer, particularly the 3' position of the sugar on the 3' terminal nucleotide. Nucleotide oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleotide oligomers, both the sugar and the internucleoside linkage, i.e., the backbone, are replaced with groups. Methods for making and using these nucleotide oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In other embodiments, a single stranded modified nucleic acid molecule (e.g., a nucleic acid molecule comprising a phosphorothioate backbone and 2'-OMe sugar modifications is conjugated to cholesterol.

In some embodiments, the disclosure is used to treat neoplasias. In other embodiments, the disclosure is used to treat cancer. In yet other embodiments, the cancer is lung cancer.

Lung cancer is a cancer of the lower respiratory tract. Examples of lower respiratory tract cancers include, but are not limited to, small cell lung carcinoma, such as squamous cell carcinoma, adenocarcinoma of the lung, large cell lung carcinoma, sarcomatoid carcinoma, carcinoid cancers of the lung, and salivary gland-like carcinoma; small cell carcinomas, such as combined small cell carcinoma; non-carcinomas, such as sarcoma, lymphoma, immature teratoma, and melanoma; pancoast tumor; and solitary pulmonary nodule.

In some embodiments, the disclosure is used to treat neoplasias. In other embodiments, the disclosure is used to treat cancer. In yet other embodiments, the cancer is stomach cancer. Stomach cancer is a cancer of the upper gastrointestinal tract. Examples of upper gastrointestinal tract cancers include, but are not limited to, cancers of the esophagus, such as squamous cell carcinoma, adenocarcinoma; cancers of the stomach, such as gastric carcinoma, signet ring cell carcinoma, gastric lymphoma, MALT lymphoma, and linitis plastica.

In some embodiments, the disclosure is used to treat neoplasias. In other embodiments, the disclosure is used to treat cancer. In yet other embodiments, the cancer is cervical cancer.

Cervical cancer is a cancer of the uterus. Examples of cervical cancers include, but are not limited to, squamous cell carcinoma and cervical intraepithelial neoplasia.

a. Delivery of Nucleotide Oligomers A microRNA of the disclosure, which may be in the mature or hairpin form, may be provided as a naked oligonucleotide that is capable of entering a tumor cell. In some cases, it may be desirable to utilize a formulation that aids in the delivery of a microRNA or other nucleotide oligomer to cells (see, e.g., U.S. Pat. Nos. 5,656,61 1, 5,753,613, 5,785,992, 6,120,798, 6,221,959, 6,346,613, and 6,353,055, each of which is hereby incorporated by reference).

In some examples, the microRNA composition is at least partially crystalline, uniformly crystalline, and/or anhydrous (e.g., less than 80, 50, 30, 20, or 10% water). In another example, the microRNA composition is in an aqueous phase, e.g., in a solution that includes water. The aqueous phase or the crystalline compositions can be incorporated into a delivery vehicle, e.g., a liposome (particularly for the aqueous phase), or a particle (e.g., a microparticle as can be appropriate for a crystalline composition). Generally, the microRNA composition is formulated in a manner that is compatible with the intended method of administration. A microRNA composition can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as $Mg^{2+}$), salts, and RNAse inhibitors (e.g., a broad specificity RNAse inhibitor, such as RNAsin). In one embodiment, the microRNA composition includes another microRNA, e.g., a second microRNA composition (e.g., a microRNA that is distinct from the first). Still other preparations can include at least three, five, ten, twenty, fifty, or a hundred or more different oligonucleotide species.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well-known examples of delivery vehicles that may be used to deliver nucleic acids of the disclosure.

A nucleic acid of the disclosure may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008, 336, 6,077,835, 5,972,901, 6,200,801, and 5,972,900, which are incorporated by reference for those aspects.

The nucleic acids may also be administered in combination with a cationic amine such as poly (L-lysine). Nucleic acids may also be conjugated to a chemical moiety, such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver.

Additionally, the molecules may be delivered using a sustained-release system, such as semipermeable matrices of solid polymers containing the therapeutic agent. Various forms of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Nucleic acids may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

b. Polynucleotide Therapy

Polynucleotide therapy featuring a polynucleotide encoding a microRNA is another therapeutic approach for inhibiting neoplasia in a subject. Expression vectors encoding the microRNAs can be delivered to cells of a subject for the treatment or prevention of a neoplasia. The nucleic acid molecules must be delivered to the cells of a subject in a form in which they can be taken up and are advantageously expressed so that therapeutically effective levels can be achieved.

Methods for delivery of the polynucleotides to the cell according to the disclosure include using a delivery system, such as liposomes, polymers, microspheres, gene therapy vectors, and naked DNA vectors.

MicroRNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., BACs and YACs). One of skill in the art would be well equipped to construct a vector through standard recombinant techniques, which are described in Sambrook et al., 1989 and Ausubel et al., 1996, both incorporated herein by reference. In addition to encoding a modified polypeptide such as modified gelonin, a vector may encode non-modified polypeptide sequences such as a tag or targeting molecule. A targeting molecule is one that directs the desired nucleic acid to a particular organ, tissue, cell, or other location in a subject's body.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71 :6641-6649, 1997; Naldini et al., Science 272:263-267, 1996; and Miyoshi et al., Proc. Natl. Acad. Sci. U.S.A. 94:10319, 1997). For example, a polynucleotide encoding a microRNA molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244: 1275-1281, 1989; Eglitis et al., BioTechniques 6:608-614, 1988; Tolstoshev et al., Current Opinion in Biotechnology 1 :55-61, 1990; Sharp, The Lancet 337:1277-1278, 1991; Cornetta et al., Nucleic Acid Research and Molecular Biology 36:31 1-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No.5,399,346).

Other suitable methods for nucleic acid delivery to effect expression of compositions of the present disclosure are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Microrna expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. For any particular subject, the specific dosage regimes should be adjusted over time according to the individual need and the professional judgment of the person administering or supervising the administration of the compositions.

c. Delivery to the Central Nervous System

Several methods can be used to deliver a micro RNA to neoplastic cells. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain, such as the substantia nigra, cortex, hippocampus, striatum, or globus pallidus. The RNA silencing agent can be delivered into multiple regions of the central nervous system (such as into multiple regions of the brain, and/or into the spinal cord). The RNA silencing agent can be delivered into diffuse regions of the brain, such as the cortex.

Alternatively, the miR can be delivered by way of a cannula or other delivery device having one end implanted in regions of the brain, such as the substantia nigra, cortex, hippocampus, striatum, or globus pallidus. The cannula can be connected to a reservoir of nucleotides encoding miRs, expression vectors containing the miR of interest, or other delivery agents containing these miRs. The flow or delivery can be mediated by a pump, such as an osmotic pump or minipump. The pump and reservoir can be implanted in an area distant from the tissue, where delivery is effected by a conduit leading from the pump or reservoir to the site of release. Devices for delivery to the brain are described, for example, in U.S. Pat. Nos. 6,093,180, and 5,814,014.

If necessary, miR2 can be further modified such that it is capable of traversing the blood brain barrier. For example, the miR, or expression vectors containing the miR, can be conjugated to a molecule that enables the agent to traverse the barrier. Such modified miRs can be administered by any desired method, such as by intraventricular or intramuscular injection, or by pulmonary delivery, for example. The conjugate moiety can be a small molecule that, for instance, targets a particular receptor or is capable of inserting itself into the membrane and being absorbed by endocytic pathways. Thus, small molecules based on adamantanes, polyaromatic hydrocarbons such as napthalenes, phenanthrenes, or pyrenes, macrocyles, steroids, or other chemical scaffolds, are all potential conjugates for traversing the blood brain barrier (for example see Bazylak and Nagels, 2002; Spasov et al., 1998; Tsuzuki et al., 1994; U.S. Pat. No. 6,656,450).

Other conjugate moieties can be based on cationic polymers. Studies have demonstrated that cationic polymers such as cationic albumin can greatly enhance delivery to the brain (Lu et. al., 2005). Given the benefits of these molecules, the conjugated moieties can be cationic polymers such as polyethyleneimine, dendrimers, poly(alkylpyridinium) salts, or cationic albumin.

Additionally, constructs containing miR2 can be encapsulated in vesicles or nanocontainers capable of transversing the blood brain barrier, permitting delivery via a transvascular approach. In such cases, a peptidomimetic mAb, such as one against the transferrin receptor can be used as a molecular "Trojan horse" to ferry any vesicle or nanocontainer containing miR2 across the BBB. Recently, great progress has been made in brain delivery by combining the antibody targeting technology with siRNA encapsulation within liposomes (Kroll and Neuwelt, 1998). If the outer surface of the delivery vehicle can be further modified with a long-circulating agent, this makes it stable in blood with prolonged blood residence times. The modification of delivery vehicles with a hydrophilic polymer as the long-circulating agent is known to enable to prolong the half-life of the delivery vehicle in the blood. Examples of the hydrophilic polymer include polyethylene glycol, polymethylethylene glycol, polyhydroxypropylene glycol, polypropylene glycol, polymethylpropylene glycol and polyhydroxypropylene oxide. In one embodiment, a hydrophilic polymer is polyethylene glycol. Glycosaminoglycans, such as hyaluronic acid, can also be used as long-circulating agents. If the tips of of a long-circulating agent are conjugated with a BBB molecular "Trojan horse", such as anti-transferrin receptor antibody, this immunoliposome is effectively delivered across the BBB. This system has been used to deliver reporter genes with success in the rat, mice, and monkey brains (Fields and Howley, 1996; Shi et al., 2001; Shi et al., 2001; Zhang et al., 2003; Zhu et al., 2003). Recently, this technology has also been used to deliver shRNAs to target specific genes in brain tumors in mice as well as monkeys (Biggerstaff and Petersen, 2003; Miller et al., 2004).

Additional means of facilitating delivery involves viral glycoproteins, which are capable of transducing their cargo across the blood brain barrier and targeting cells of the CNS. Thus, miR2, fragments, expression vectors, or liposome or nanoparticle delivery vehicles can be tagged with such viral glycoproteins or nucleotides encoding them. For example, glycoproteins of adeno-associated and rabies viruses have been shown capable of efficiently delivering tagged DNA, siRNA, and peptides across the blood brain barrier to cells of the CNS (for example, see US Pat. Pub. Nos. US2007/012152 and US2009/0162332).

III. Radiation Therapy

Radiation causes DNA damage, and induces apoptosis in exposed cells as a result. Radiation therapy has been used extensively in cancer treatment and includes what are commonly known as γ-rays, X-rays (external beam), and the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Typical dosage ranges for X-rays range from daily doses of 50, 75, 100, 150 or 200 roentgens for prolonged periods of time (3 to 4 wk), to single doses of 1000, 2000, 3000, 4000, 5000 or 6000 roentgens. Dosage ranges for radioisotopes vary widely, and depend on the half-life of the isotope and the strength and type of radiation emitted.

In accordance with the present disclosure, the amount of radiation may be applied in a fractionated regimen—multiple doses adding to a total dose of about 40 to 60 Gy. More particularly, the regimen may comprise fractionated individual doses of 2 Gy (200 rads). In a specific embodiment, x-irradiation is employed.

The terms "contacted" and "exposed," when applied to a cell, are used herein to describe the process by which a radiotherapy is delivered to a target cell or placed in direct juxtaposition with the target cell. To achieve cell killing or apoptosis, the radiation is delivered to a cell in combination with a vitamin D3 compound in an amount effective to kill the cell or induce apoptosis.

The two main types of radiation include external beam radiation and delivery of radioactive isotope internally. With regard to the latter, it is not uncommon to use a targeting agent, such as a monoclonal antibody, that carries the radionuclide to the hyperproliferative tissue. Suitable radioactive isotopes include astatine$^{211}$, $^{14}$carbon, $^{51}$chromium, $^{36}$chlorine , $^{57}$cobalt, $^{58}$cobalt, Copper $^{67}$, $^{152}$Eu, gallium$^{67}$, $^{3}$hydrogen, iodine$^{123}$, iodine125, iodine131, indium111, 59iron, 32phosphorus, rhenium186, rhenium188, $^{75}$selenium, $^{35}$sulphur, technicium$^{99m}$ and/or yttrium$^{90}$.

VI. Combinatorial Therapy with miR2 as Well as the miR-548 Family and Radiation

In order to create a more effective cancer therapy, the scope of this disclosure encompasses the administration miR2 in combination with radiotherapy for the treatment of neoplasias such as cancer. In particular, the therapy is designed to induce apoptosis (cell death) in cancer cells, although reducing the incidence or number of metastases, and reducing tumor size also are contemplated. Tumor cell resistance to radiotherapy agents represents a major problem in clinical oncology. Thus, in the context of the present disclosure, it also is contemplated that miR2 and the miR-548 family therapy could be used on radiation resistant lines to improve the efficacy of the latter.

This process may involve contacting the hyperproliferative cells with the radiation and miR2 at the same time. Alternatively, miR2 and the miR-548 family therapy may precede or follow the radiation by intervals ranging from minutes to weeks. In embodiments where the radiation and miR2 as well as the miR-548 family are applied at distinct times, one would generally ensure that a significant period of time did not expire between the time of each delivery, such that the miR2 as well as the miR-548 family and radiation would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Administration of miR2 and the miR-548 family, defined in the present disclosure, to a patient will follow general protocols for the administration of chemotherapeutics, taking into account the toxicity, if any. It is expected that the treatment cycles would be repeated as necessary.

IV. Other Cancer Therapies

In accordance with the present disclosure, it also is envisioned that miR2 and the miR-548 family therapy may further be combined with other cancer therapies. Such therapies include classic chemotherapy or gene therapy, both of which in some embodiments can improve the efficacy of therapeutic treatment of neoplasias. These therapies are described below.

a. Chemotherapy

Several anti-cancer therapeutics exert their cytotoxic effects by damaging DNA, inhibiting cell cycle progression, or inducing apoptosis, either directly or indirectly.

Cancer therapies include a variety of combination therapies with both chemical and radiation based treatments. Combination chemotherapies include but are not limited to, for example, adriamycin, anthracycline, bevacizumab, cisplatin (CDDP), carboplatin, etoposide (VP16), irinotecan, mitoxantrone, procarbazine, mechlorethamine, cyclophosphamide, camptothecin, COX-2 inhibitors (e.g., celecoxib) ifosfamide, melphalan, chlorambucil, busulfan, nitrosurea, dactinomycin, daunorubicin, doxorubicin (adriamycin), bleomycin, plicomycin, mitomycin, tamoxifen, raloxifene, estrogen receptor binding agents, taxol, taxotere, gemcitabien, navelbine, farnesyl-protein transferase inhibitors, transplatinum, 5-fluorouracil, vincristin, vinblastin and methotrexate, or any analog or derivative variant of the foregoing.

b. Gene or Peptide Therapy

In yet another embodiment, the additional treatment is a therapy in which a therapeutic polynucleotide or polypeptide is administered before, after, or at the same time as miR2 and/or radiation. Delivery of a vector, polynucleotide or polypeptide designed to alter the expression, complex formation, or activity of any gene, protein or protein complex capable of inducing DNA damage, inhibiting cell cycle progression, or inducing apoptosis in neoplastic cells in conjunction with miR2 and the miR-548 family is expected to have a combined sensitizing effect on target tissues.

V. Pharmaceutical Compositions

As reported herein, a reduction in the expression of specific microRNAs in certain neoplastic cells is associated with various cancers in humans. Accordingly, the disclosure provides therapeutic compositions that increase the expression of microRNAs described herein for the treatment or prevention of a neoplasm. In one embodiment, the present disclosure provides a pharmaceutical composition comprising a microRNA of the disclosure or a nucleic acid molecule encoding a microRNA of the disclosure. If desired, the nucleic acid molecule is administered in combination with a chemotherapeutic agent. In another embodiment, a recombinant microRNA or a polynucleotide encoding such a microRNA, is administered to reduce the radiosensitivity, sensitivity, growth, survival or proliferation of a neoplastic cell or to increase apoptosis of a neoplastic cell. Polynucleotides of the disclosure may be administered as part of a pharmaceutical composition. The compositions should be sterile and contain a therapeutically effective amount of a microRNA or nucleic acid molecule encoding a microRNA in a unit of weight or volume suitable for administration to a subject. A recombinant microRNA or a nucleic acid molecule encoding a microRNA described herein may be administered within a pharmaceutically-acceptable diluent, carrier, or excipient, in unit dosage form. Conventional pharmaceutical practice may be employed to provide suitable formulations or compositions to administer the compounds to patients suffering from a neoplasia. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene- polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a nucleotide oligomer of the disclosure is likely to depend on such variables as the type and extent of the disorder, the overall health status of the particular patient, the formulation of the compound excipients, and its route of administration.

With respect to a subject having a neoplastic disease or disorder, an effective amount is sufficient to stabilize, slow, or reduce the proliferation of the neoplasm. Generally, doses of active polynucleotide compositions of the present disclosure would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels a microRNA of the disclosure or of a polynucleotide encoding such a microRNA.

Accordingly, the present disclosure provides methods of treating disease and/or disorders or symptoms thereof which comprise administering a therapeutically effective amount of a composition comprising a microRNA described herein to a subject (e.g., a mammal, such as a human). Thus, one embodiment is a method of treating a subject suffering from or susceptible to a neoplastic disease or disorder or symptom thereof. The method includes the step of administering to the mammal a therapeutic amount of a microRNA or nucleic acid encoding such a microRNA herein sufficient to treat the neoplastic disease or disorder or symptom thereof, under conditions such that the disease or disorder is treated.

The methods herein include administering to the subject (including a subject identified as in need of such treatment) an effective amount of a compound described herein, or a composition described herein to prevent, treat, stabilize, or reduce the growth or survival of a neoplasia in a subject in need thereof. Identifying a subject in need of such treatment can be in the judgment of a subject or a health care professional and can be subjective (e.g. opinion) or objective (e.g. measurable by a test or diagnostic method).

The therapeutic methods of the disclosure (which include prophylactic treatment) in general comprise administration of a therapeutically effective amount of the agents herein, such as a microRNA or a nucleic acid encoding such a microRNA herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (e.g., altered mi2 expression or a neoplasia associated with an alteration in miR2 and the miR-548 family or as defined herein), condition (e.g., resistance to radiotherapy), family history, and the like. The compounds herein may be also used in the treatment of any other disorders in which miR2 and the miR-548 family dysregulation may be implicated.

IX. Therapy

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of neoplasia being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength. Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As described above, if desired, treatment with a microRNA or a polynucleotide encoding such a microRNA may be combined with therapies for the treatment of proliferative disease (e.g., radiotherapy, surgery, or chemotherapy). For any of the methods of application described above, microRNA of the disclosure is desirably administered intravenously or is applied to the site of neoplasia (e.g., by injection, transfection, etc.).

EXAMPLE

The survival rates of patients afflicted with stomach or lung cancer are less than 15% after five years. Although surgery and anticancer therapies do induce growth inhibition in these cancerous cells, the inhibition is often slight and effectiveness does not necessarily translate well to patient therapy. A miRNA, miR2, which is located in intron 4 of the FHIT gene has been identified. Overexpression of miR2 is capable of reducing tumor cell growth within animal models of various cancers, which is surprising given its variable expression levels in different cancer types as well as cell lines of the same cancer type.

As discussed in the examples, forced overexpression of miR2 within various cancer cell lines through viral transfection reduced tumor size by as much as 70% compared to control transfections.

The introns of FHIT gene were extracted from UCSC genome browser. The candidate miRNAs were obtained with the following three steps: (i) The homologous sequences were searched with known miRNAs (miRBase release 13), fRNAdb3, and NONCODE2 using blast; (ii) The candidate pre-miRNAs were predicted using SVM bagging, a method proposed for an initio prediction of pre-miRNAs in genomes; and (iii) The crossover sequences of homologous sequences and predicted candidate pre-miRNAs were taken as our candidate miRNAs.

Total RNA was extracted from the cultured cells using Trizol (Invitrogen, Carlsbad, Calif., USA) and small RNA by using a miRNeasy Mini Kit (Qiagen, Valencia, Calif., USA) according to the manufacturer's instructions. The concentration of RNA was quantified by the absorbance at 260 nm. RNA was polyadenylated by poly(A) polymerase (New England Biolabs) first. Of the polyadenylation reaction, 50 µL were set up with 10 µg of total RNA and 10 U of poly(A) polymerase according to the manufacturer's protocol. The reaction was incubated at 37° C. for 1 hr. After incubation, poly(A)-tailed RNA was recovered by phenol/chloroform extraction and ethanol precipitation. Reverse transcription was performed using 2 µg total RNA or poly(A)-tailed RNA and 2 µg of RT primer (TGCGAGCACAGAATTAATAC-GACTCACT ATAGGd(T)$_{18}$) (SEQ ID NO:5) with 200U of SuperScript III (Invitrogen). A 2-µg aliquot of RNA (10 µL of total volume) was incubated with 2 µL of RT primer and 1 µL of dNTP mix (10 mM each) at 65° C. for 5 min to remove any RNA secondary structure. The reactions were chilled on ice for at least 5 min and remaining reagents (10×RT buffer, MgCl$_2$, dithiothreitol[DTT], RNase Out and SuperScript III) were added as specified in the SuperScript III protocol and the reaction proceeded for 50 min at 50° C. Finally, the reverse transcriptase was inactivated by a 5-min incubation at 85° C. The minus reverse transcription control was treated identically except that the reactions lacked SuperScript III and primer.

Figure 2:
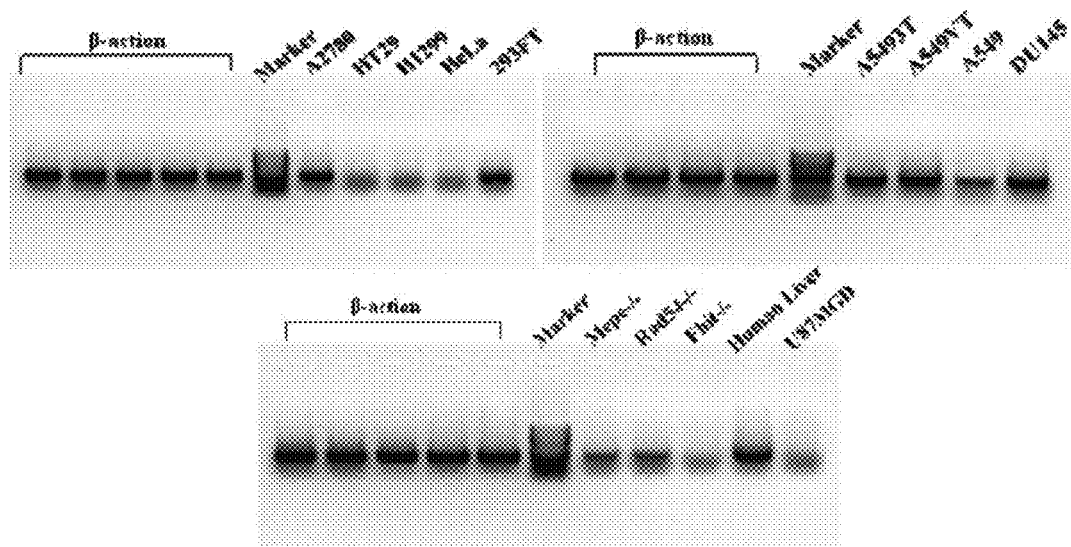
FIG. 2 illustrates the expression of FHIT in different cell lines.
Figure 3:
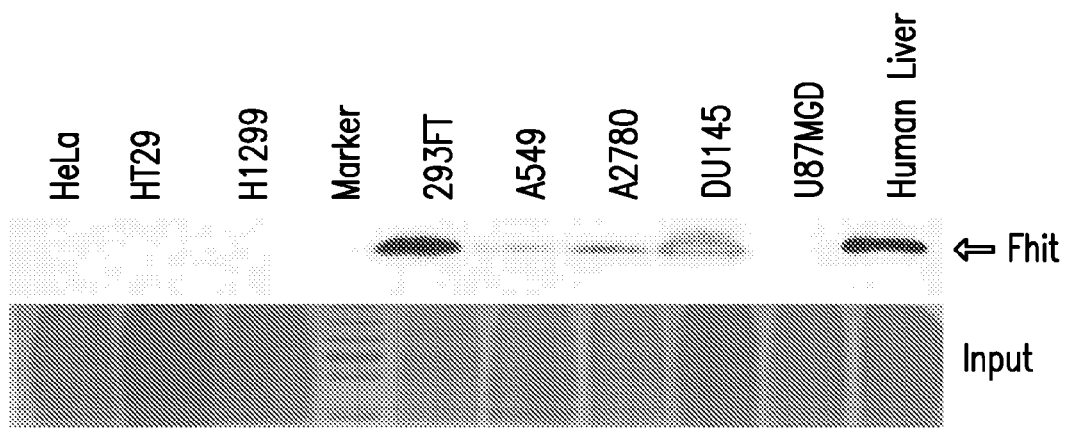
FIG. 3 illustrates the expression of FHIT protein in different cell lines.
Figure 4:
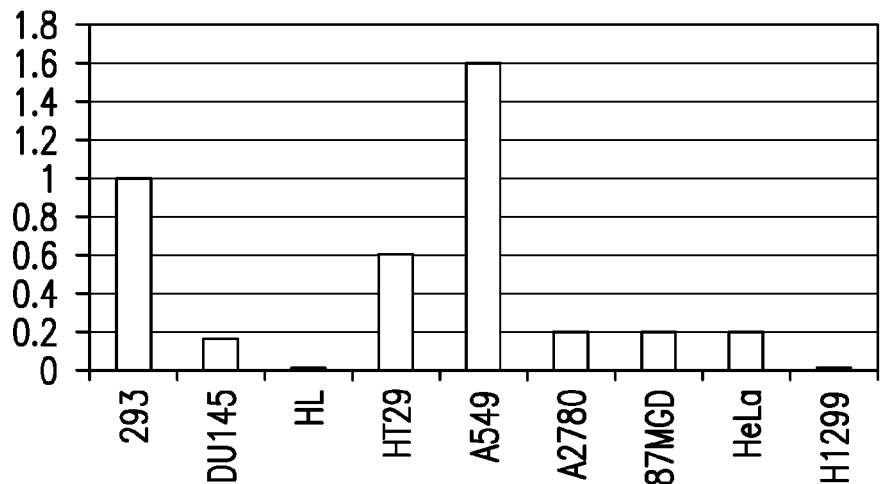
FIG. 4 illustrates the expression of miR2 in different cell lines.

Prediction of the novel miRNAs in the intron of the FHIT gene was shown in FIG. 1. Analysis of FHIT mRNA and protein in several cancer and normal cell lines revealed that expression levels do not correspond with those of miR2 (FIG. 2-4). For example, FHIT expression levels in the lung cancer cell line A549 was much lower than in HEK293 cells while the opposite was observed with miR2 expression.

Figure 5:
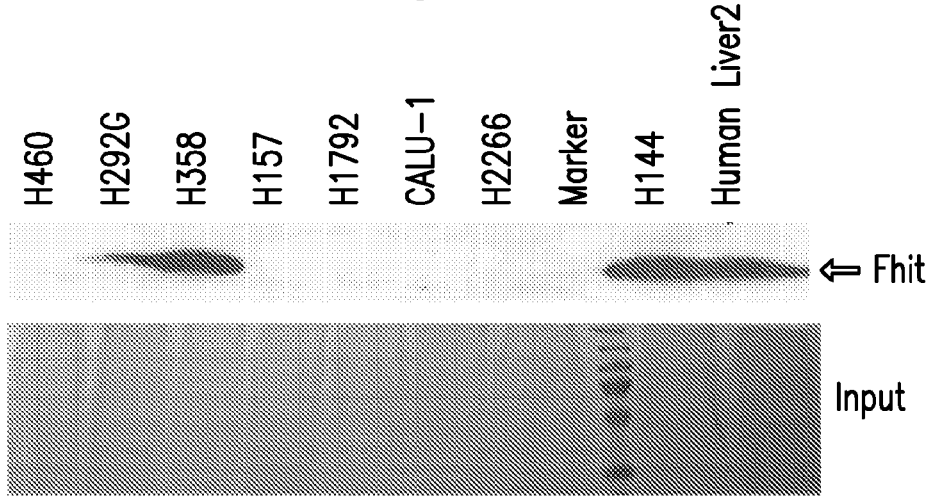
FIG. 5 illustrates the expression of FHIT protein in cell lines transfected with miR2 expression vector. Cells ending with a "VT" was transfected with empty vector alone, 1 or 1T was PCR with the control probes and 3 or 3T was PCR with the miR2 probes, which demonstrates the miR2 is a real miRNA existed in the human cells.
Figure 6:
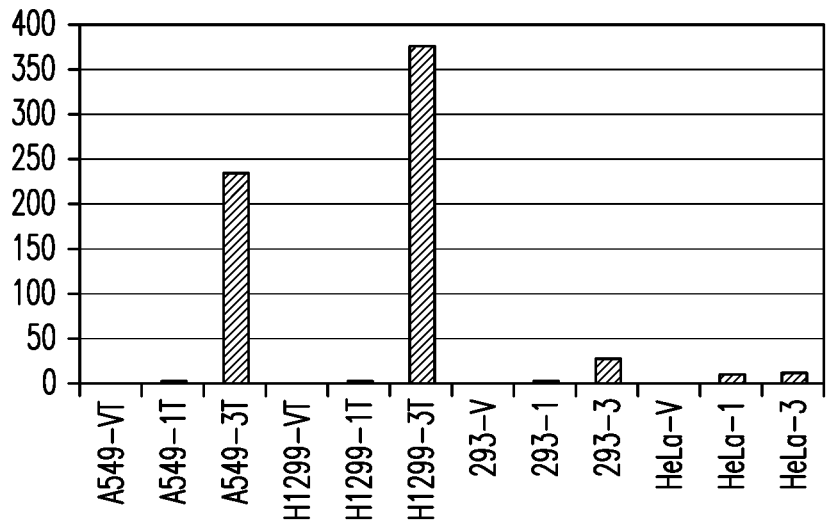
FIG. 6 illustrates the expression of miR2 in cell lines transfected with miR2 expression vector. Cells ending with a "-v" or "-vt" were transfected with empty vector alone.

To construct a plasmid expressing miR2, a DNA fragment carrying pri-miR2 was amplified using genomic DNA from a healthy blood donor as a template. The amplified fragment was first cloned into a PCR cloning vector and subsequently into the lentiviral vector: pCDH-CMV-MCS-EF1-copGFP (System Biosciences, Mountain View, Calif., USA) at the EcoR I and BamH I sites. 293FT cells were directly transfected with the lentiviral vector-miR2 (pCDH-CMV-MCS-EF1-copGFP-pri-miR2) and the pCDH-CMV-MCS-EF1-copGFP vector alone (System Biosciences) by using Lipofectamine 2000 (Invitrogen) according to the manufacturer's instructions. The expressions of GFP protein were observed at 48 hr. The lung cell lines A549 and H1299, as well as HeLa and 293FT were transduced by the packaged lentivirus. Briefly, approximately 4×10$^6$ 293FT cells were seeded in a 100 mm dish for 3-4 hr. The lentiviral vector-miR2 or lentiviral vector alone (3 µg) and pPACKH1 Packaging Plasmid Mix (30 µg) (System Biosciences, Mountain View, Calif., USA) were formed complex with Lipofectamine™ 2000 and transfected to the 293FT cells. The culture medium containing the packaged viruses was harvested at 48 hr after transfection and spun at 4° C., 3000 rpm for 10 min. The supernatant was collected and polybrene was added to the final concentration 8 µg/ml. The mixture (5 ml) was added to the cell culture in a 100 mm dish with 5 ml of medium. The transduced cells were harvested after 72-96 hr post-infection for further experiments. Reverse transcriptase PCR was used to verify efficiency and levels of miR2 expression in transfected cells (FIG. 6: 1T was used with the control probe and 3T was used with the miR2 probe). Western blots were also performed on cell lysates to assay the effects of miR2 on FHIT expression. Overexpression of miR2 did not have any effect on FHIT expression (FIG. 5).

Figure 7:
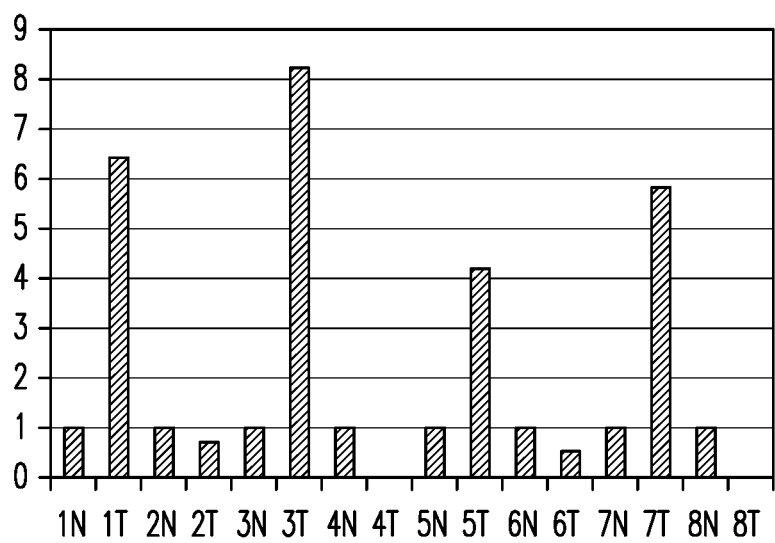
FIG. 7 illustrates the variable expressivity of miR2 in human lung cancer samples.
Figure 8:
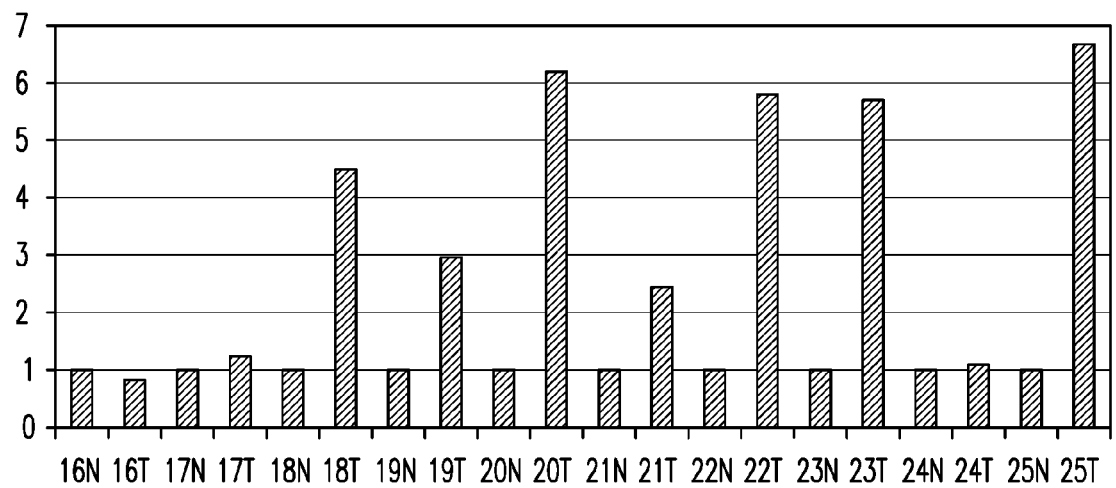
FIG. 8 illustrates the variable expressivity of miR2 in human stomach cancer samples.
Figure 9:
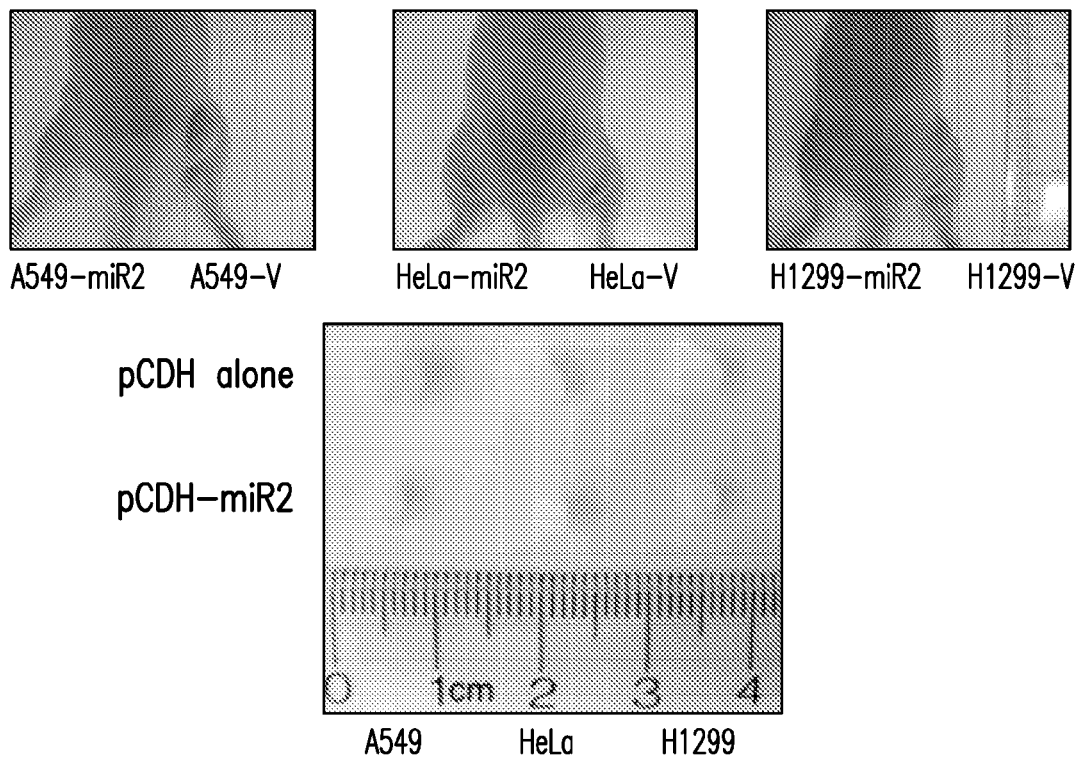
FIG. 9 illustrates the tumor size of mouse xenograft models of various cancer cell lines transfected with a miR2 expression vector.
Figure 10:
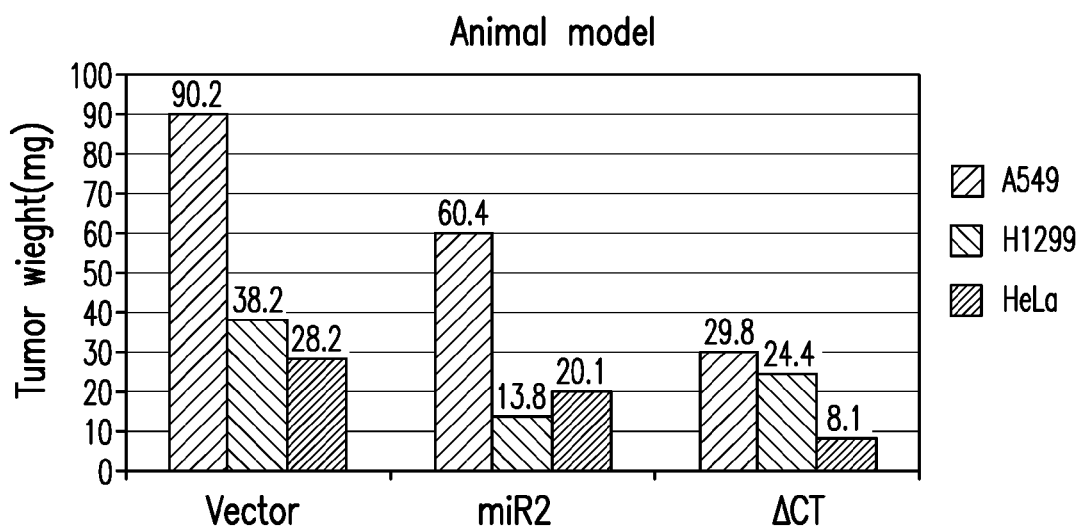
FIG. 10 illustrates the change in tumor mass of mouse xenograft models of various cancer cell lines transfected with a miR2 expression vector. $\Delta$CT refers to the difference in tumor cell mass between empty vector and miR2-containing vector.
Figure 11:
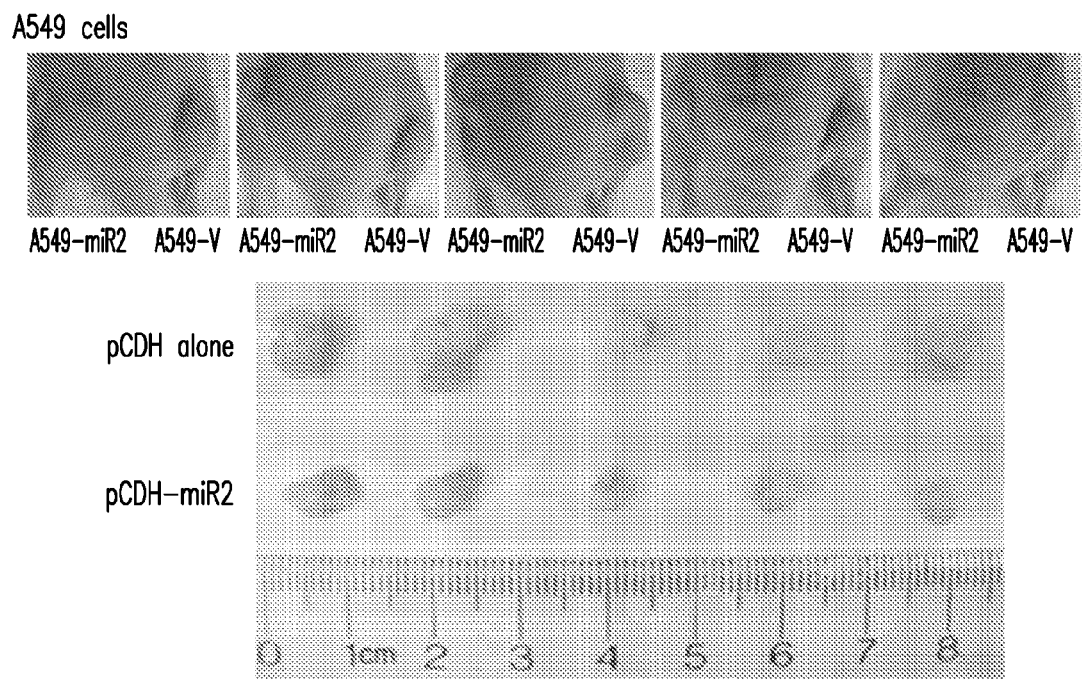
FIG. 11 illustrates the tumor size of mouse xenograft models of various cancer cell lines transfected with A549 lung cancer cells.
Figure 12:
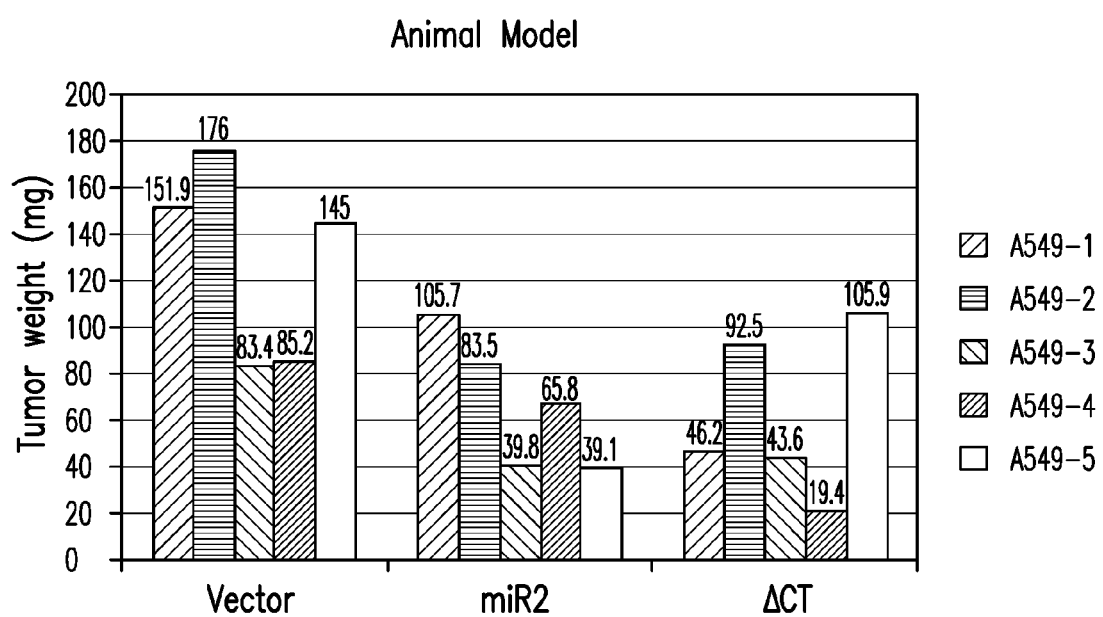
FIG. 12 illustrates the change in tumor mass of mouse xenograft models of various cancer cell lines transfected with A549 lung cancer cells. $\Delta$CT refers to the difference in tumor cell mass between empty vector and miR2-containing vector.
Figure 13:
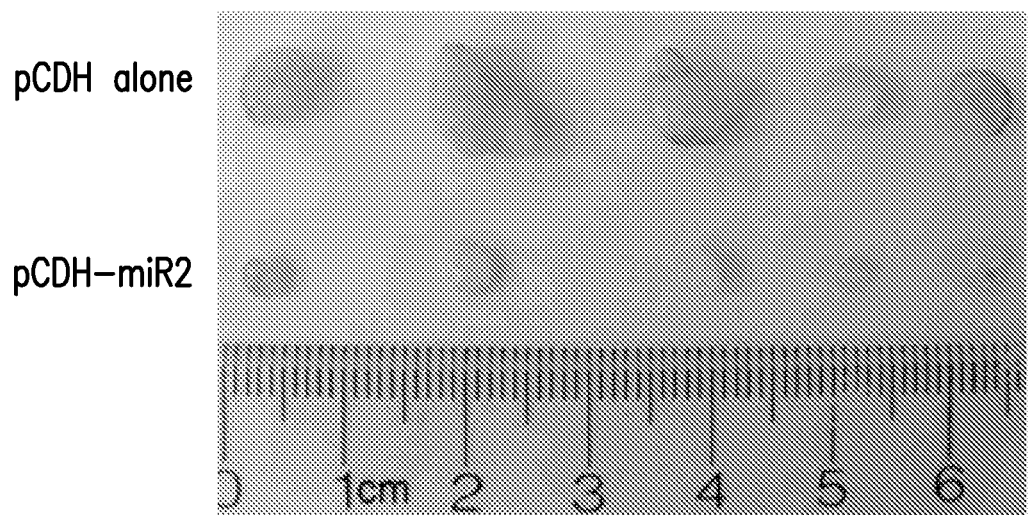
FIG. 13 illustrates the tumor size of mouse xenograft models of various cancer cell lines transfected with H1299 lung cancer cells.

Because microRNAs have been implicated in cancer progression, the expression of miR2 in human lung and stomach cancer samples was examined. The expression of miR2 in human lung and stomach cancer samples was found to vary significantly between individual samples (FIGS. 7, 8), suggesting a role for miR2 in cancer progression.

To further examine a potential inhibitory role of miR2 on neoplastic cells, the lung cancer cell lines A549 and H1299 as well as HeLa cells were transfected with control expression vectors or one containing miR2. Nude mice were then subcutaneously injected with with 3×10$^6$ A549, H1299 and HeLa cells transfected with vector alone (pCDH-CMV-MCS-EF1-copGFP, right legs) or with the vector encoding miR2 (left hind legs) to generate mouse xenograft models of lung and cervical cancer. The mice were sacrificed at 25 days (A549 cells) or 30 days (H1299 cells) after the tumor cell inoculation and the tumors were removed and weighed. Transfection of miR2 into either lung cancer cell line or HeLa cells inhibited the growth of tumors in mouse xenograft models (FIGS. 9-13), demonstrating a role for miR2 in the inhibition of neoplastic growth and tumor progression.

Cyclin D1 and Her2 are the Predicted Targets of the miR-548 Family

Cyclin-D1 is an onco-protein that is encoded by the CCND1 gene and located at the human chromosome 11 (11q13). The protein encoded by this gene belongs to the highly conserved cyclin family, whose members are characterized by a dramatic periodicity in protein abundance throughout the cell cycle. Cyclin D1 is required for cell cycle G1/S transition. Cyclin D1 with its partner CDKs phophorylates Rb, an important tumor suppressor and, therefore, inactivates Rb. Amplification and over-expression of the CCND1 gene is observed frequently in a variety of tumors and is associated with tumor progression.

Her2 (also known as ErbB-2), another onco-protein, stands for "Human Epidermal growth factor Receptor 2" and is a member of the epidermal growth factor receptor (EGFR) family. Her2 is encoded by the ERBB2 gene and located at the human chromosome 17 (17g21-q22). Her2 is a cell membrane surface-bound receptor tyrosine kinase and is normally involved in the signal transduction pathways leading to cell growth and differentiation. Amplification and over-expression of these genes are observed frequently in a variety of tumors and are associated with tumor progression.

Figure 14A:
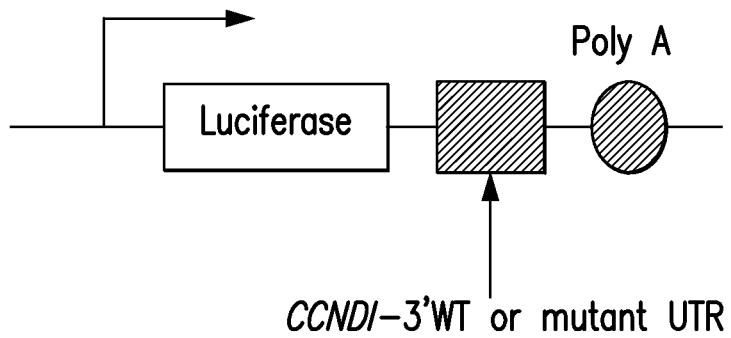
FIG. 14 shows data suggesting CCND1 as a target of has-miR2. (A) The design of the leuciferase-assay vector. (B) The effects of different miRNAs on the leuciferase activities. 293T cells were transfected with pIREB (encoding the full-length of 3'-UTR of CCND1) without miRNA, pIREB+miR-758, or pIREB+miR-2*. The leuciferase activities were detected. (C) The effects of has-miR-2* on the leuciferase activities of the different sites of CCND1 3'-UTR: number 1 is at the position of 469-474, number 2 at 911-917, number 3 at 1416-1422 and number 4 at 3138-3144 of CCND1-3' UTR. (D) Compare Cyclin D1 levels in 293T cells transfected with either vector alone or the vector encoding has-miR-2. GAPDH was used as an internal loading control.
Figure 14B:
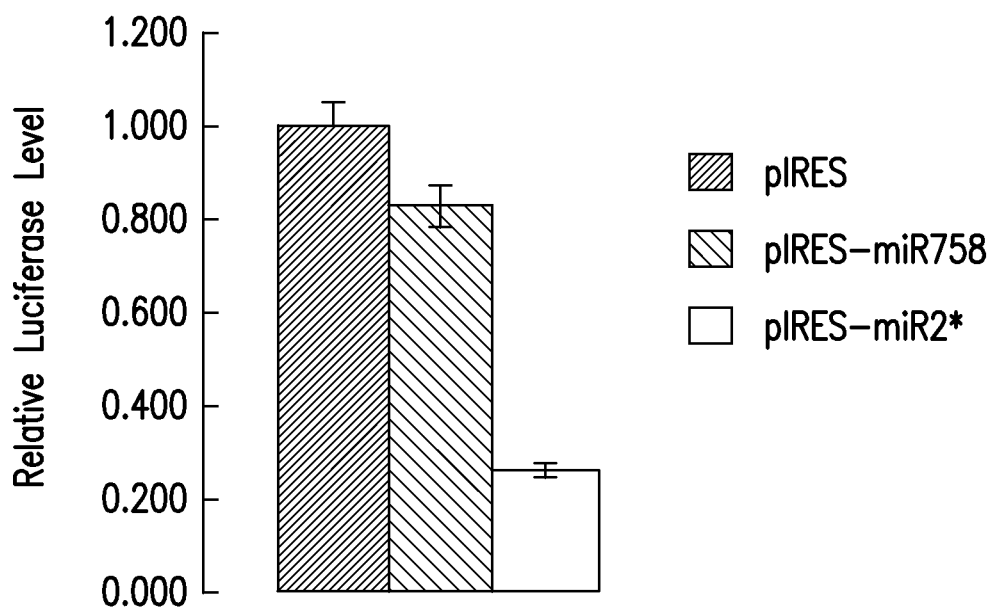

After performing a database search, there are potentially 4 binding sites found for hsa-miR-2 in the 3'-UTR of CCND1 (number 1 is at the position of 469-474, number 2 at 911-917, number 3 at 1416-1422 and number 4 at 3138-3144 of CCND1-3' UTR). By using the leuciferase, mutation overexpression and Western blot assays, one of the four sites were identified (number 2 at 911-917 of CCND1-3' UTR) as the real binding site for hsa-miR2 and confirmed that the CCND1 gene is a target of hsa-miR2 (FIG. 14). These results indicate that CCND1 (Cyclin D1) is a target of has-miR-2. Since the seed region of has-miR2 to target CCND1 is relatively conservative in the miR-548 family, CCND1 should be a common target of the miR-548 family.

The invention claimed is:

1. A synthesized nucleic acid molecule of less than 50 nucleotides or base pairs comprising nucleic acid sequences having at least 90% identity to SEQ ID NO: 4 comprising a first nucleotide sequence AAAX (SEQ ID NO:7) wherein X is G, and a second nucleotide sequence UUUG (SEQ ID NO:9), provided that any U individually and independently may be uracil or thymine wherein the first and the second sequences are separated by 11 nucleotides;
   wherein the synthesized nucleic acid has at least one modified linkage, at least one modified sugar moiety, or one modified nucleotide base.

2. The synthesized nucleic acid molecule of claim 1 wherein the nucleic acid molecule comprises a nucleotide sequence having SEQ ID NO: 2, 4, 23, or 53.

3. The synthesized nucleic acid molecule of claim 1 wherein the nucleic acid molecule consisting essentially of a nucleotide sequence having SEQ ID NO: 2, 4, 23, or 53.

4. A recombinant viral vector comprising a nucleotide sequence having at least 90% identity to SEQ ID NO: 4 provided that any U individually and independently may be uracil or thymine.

5. An isolated host cell comprising a recombinant viral vector comprising a nucleotide sequence having at least 90% identity to SEQ ID NO: 4 provided that any U individually and independently may be uracil or thymine.

6. A pharmaceutical composition comprising a synthesized nucleic acid as in claim 1 and a pharmaceutically acceptable excipient.

7. The synthesized nucleic acid molecule of claim 1 wherein the first nucleotide sequence comprise AAAAXU (SEQ ID NO: 5), wherein X is G, and the second nucleotide sequence comprises UUUUGY (SEQ ID NO: 17), wherein Y is U or C, provided that any U individually and independently may be uracil or thymine, wherein the first and the second sequences are separated by 9 nucleotides.

8. The synthesized nucleic acid molecule of claim 1 comprising at least one phosphorothioate linkage.

9. The synthesized nucleic acid molecule of claim 1 comprising at least one at least one modified sugar moiety selected from a 2'-O-methyl, 2'-fluorine, 2'-O-methoxyethyl, 2'-O-aminopropyl, and 2'-amino modification.

10. The synthesized nucleic acid molecule of claim 1 comprising at least one at least one base modification selected from , 5-fluorouracil, 5-bromouracil, 5-chlorouracil, 5-iodouracil, 4-acetylcytosine, 5-(carboxyhydroxymethyl) uracil, 5-carboxymethylaminoethyl-2-thiouridine, 5-carboxymethylaminomethyluracil, dihydrouracil, 1-methylguanine, 1-methylinosine, 2,2-dimethylguanine, 2-methyladenine, 2-methylguanine, 3methylcytosine, 5-methylcytosine, 7-methylguanine, 5-methylaminomethyluracil, 5methoxyaminomethyl-2-thiouracil, beta-D-mannosylqueosine, 5-methoxycarboxymethyluracil, 5-methoxyuracil, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

\* \* \* \* \*